(12) United States Patent
Zawaneh et al.

(10) Patent No.: US 10,172,794 B2
(45) Date of Patent: Jan. 8, 2019

(54) CONTROLLED RELEASE DOSAGE FORM FOR ONCE DAILY ADMINISTRATION OF DIMETHYL FUMARATE

(71) Applicant: Biogen MA Inc., Cambridge, MA (US)

(72) Inventors: Peter Zawaneh, Brookline, MA (US); Shyam B. Karki, Hillsborough, NJ (US); Michael Kaufman, Lexington, MA (US); Cheuk-Yui Leung, Acton, MA (US); Jinquan Dong, Stoneham, MA (US); Ernest Quan, East Lyme, CT (US); Kalyan Vasudevan, Cambridge, MA (US)

(73) Assignee: Biogen MA Inc., Carmbridge, MA (US)

( * ) Notice: Subject to any disclaimer, the term of this patent is extended or adjusted under 35 U.S.C. 154(b) by 0 days.

(21) Appl. No.: 15/102,306

(22) PCT Filed: Dec. 12, 2014

(86) PCT No.: PCT/US2014/070058
§ 371 (c)(1),
(2) Date: Jun. 7, 2016

(87) PCT Pub. No.: WO2015/089420
PCT Pub. Date: Jun. 18, 2015

(65) Prior Publication Data
US 2016/0310419 A1    Oct. 27, 2016

Related U.S. Application Data

(60) Provisional application No. 61/916,115, filed on Dec. 13, 2013.

(51) Int. Cl.
*A61K 9/00* (2006.01)
*A61K 9/20* (2006.01)
(Continued)

(52) U.S. Cl.
CPC .......... *A61K 9/0065* (2013.01); *A61K 9/0004* (2013.01); *A61K 9/14* (2013.01);
(Continued)

(58) Field of Classification Search
None
See application file for complete search history.

(56) References Cited

U.S. PATENT DOCUMENTS

| 4,140,755 A | 2/1979 | Sheth et al. |
| 5,232,704 A | 8/1993 | Franz et al. |

(Continued)

FOREIGN PATENT DOCUMENTS

| EP | 2316430 A1 | 5/2011 | |
| EP | 2379063 B1 * | 3/2013 | .......... A61K 9/2054 |

(Continued)

OTHER PUBLICATIONS

Shashank et al., "Approaches to increase the gastric residence time: floating drug delivery systems—a review," Asian Journal of Pharmaceutical and Clinical Research, vol. 6, Issue 3, pp. 1-9, May 2013. (Year: 2013).*

(Continued)

*Primary Examiner* — Ernst V Arnold
*Assistant Examiner* — Kyung S Chang
(74) *Attorney, Agent, or Firm* — Jones Day

(57) ABSTRACT

A controlled release dosage form containing monomethyl fumarate, a compound that can be metabolized into monomethyl fumarate in vivo, or a pharmaceutically acceptable salt thereof or combinations thereof, wherein the monomethyl fumarate, a compound that can be metabolized into monomethyl fumarate in vivo, or a pharmaceutically acceptable salt thereof or combinations thereof is delivered to the subject. Also provided is a method of treating a disease or disorder (e.g., multiple sclerosis) by orally administering a controlled (Continued)

release dosage form containing monomethyl fumarate, a compound that can be metabolized into monomethyl fumarate in vivo, or a pharmaceutically acceptable salt thereof or combinations thereof, wherein the monomethyl fumarate, a compound that can be metabolized into monomethyl fumarate in vivo, or a pharmaceutically acceptable salt thereof or combinations thereof.

6 Claims, 7 Drawing Sheets

(51) Int. Cl.
    *A61K 9/28*     (2006.01)
    *A61K 31/225*     (2006.01)
    *A61P 25/00*     (2006.01)
    *A61K 9/48*     (2006.01)
    *A61K 9/50*     (2006.01)
    *A61K 31/22*     (2006.01)
    *A61K 9/14*     (2006.01)

(52) U.S. Cl.
CPC .......... *A61K 9/2027* (2013.01); *A61K 9/2031* (2013.01); *A61K 9/2054* (2013.01); *A61K 9/2086* (2013.01); *A61K 9/2846* (2013.01); *A61K 9/2853* (2013.01); *A61K 9/2866* (2013.01); *A61K 9/2886* (2013.01); *A61K 9/4808* (2013.01); *A61K 9/5026* (2013.01); *A61K 9/5031* (2013.01); *A61K 9/5042* (2013.01); *A61K 9/5047* (2013.01); *A61K 9/5073* (2013.01); *A61K 31/22* (2013.01)

(56) References Cited

U.S. PATENT DOCUMENTS

| | | | |
|---|---|---|---|
| 5,972,389 | A | 10/1999 | Shell et al. |
| 6,022,562 | A | 2/2000 | Autant et al. |
| 6,509,376 | B1 | 1/2003 | Joshi et al. |
| 6,723,340 | B2 | 4/2004 | Gusler et al. |
| 6,960,356 | B1 | 11/2005 | Talwar et al. |
| 7,682,629 | B1 | 3/2010 | Besse |
| 8,101,209 | B2 | 1/2012 | Legrand et al. |
| 8,298,574 | B2 | 10/2012 | Tsabari et al. |
| 8,927,028 | B2 | 1/2015 | Grenier et al. |
| 2004/0234601 | A1 | 11/2004 | Legrand et al. |
| 2008/0233185 | A1 | 9/2008 | Joshi et al. |

FOREIGN PATENT DOCUMENTS

| | | | | |
|---|---|---|---|---|
| EP | 2564839 A2 | 3/2013 | | |
| WO | WO-2013076216 A1 | * | 5/2013 | .......... A61K 9/5026 |
| WO | WO 2013/119677 A1 | 8/2013 | | |

OTHER PUBLICATIONS

International Search Report of International Application PCT/US2014/070058, dated Mar. 9, 2015.
Written Opinion of the International Searching Authority for International Application PCT/US2014/070058, dated Mar. 9, 2015.
International Preliminary Report on Patentability for International Patent Application No. PCT/US2014/070058, International Bureau of WIPO, Switzerland, dated Jun. 14, 2016.
Ranade et al., 2012, "Development of Bilayer Floating Tablet of Amoxicillin and Aloe vera Gel Powder for Treatment of Gastric Ulcers," AAPS PharmSciTech, 13(4):1518-1523.
Rouge et al., 1998, "Buoyancy and Drug Release Patterns of Floating Minitablets Containing Piretanide and Atenolol as Model Drugs," Pharm. Dev, Technol., 3(1):73-84.
Rouge et al., 1998, "Comparative pharmacokinetic study of a floating multiple-unit capsule, a high-density multiple-unit capsule and an immediate-release tablet containing 25 mg atenolol," Pharmaceutica Acta Helletiae, 73(1998):81-87.
Zou et al., 2007, "Design and Gamma-Scintigraphic Evaluation of a Floating and Pulsatile Drug Delivery System Based on an Impermeable Cylinder," Chem. Pharm. Bull., 55(4):580-585.
Hou et al., 2003, "Gastric Retentive Dosage Forms: A Review," Crit. Rev. Ther. Drug Carrier Syst., 20(6):459-497.
MOES, 1993, "Gastroretentive Dosage Forms," Crit. Rev. Ther. Drug Carrier Syst., 10(2):143-195.
Thitinan and McConville, 2011, "Development of a Gastroretentive Pulsatile Drug Delivery Platform," J. Pharm. Pharmacol., 64(4):505-516.
Singh and Rana, 2013, "Enhancement of Mucoadhesive Property of Polymers for Drug Delivery Applications: A Critical Review," Rev. Adhesion Adhesives, 1(2):271-290.
Lee et al., 2012, "Efficacy of Thiolated Eudragit Microspheres as an Oral Vaccine Delivery System to Induce Mucosal Immunity Against Enterotoxigenic *Escherichia coil* in Mice," Eur. J. Pharm. Biopharm., 81(1):43-48.
Alli et al., 2011, "Oral Mucoadhesive Microcamers for Controlled and Extended Release Formulations," Int. J. Life Sci. Pharma Res., 1(1):L41-L59.
Sonia and Sharma, 2011, "Chitosan and Its Derivatives for Drug Delivery Perspective," Adv. Polym. Sci., 243:23-53.
Tanero et al., 2006, "Pharmacokinetic Properties of a New Controlled-Release Formulation of Carvedilol," Am. J. Cardiol., 98(7A):5L-16L.
Waterman et al., 2009, "Extendable Core System: Development of a Single-Layer Osmotic Controlled-Release Tablet," J. Control Release, 134(3):201-206.

* cited by examiner

- 16566-89-C3 15% (15%L100) pH7.4 Flow8-1Tab – 1
- 16566-89-C3 15% (15%L100) pH7.4 Flow8-1Tab – 2
- 16566-89-C3 15% (15%L100) pH7.4 Flow8-1Tab – 3
- 16566-89-C3 15% (15%L100) pH7.4 Flow8-1Tab – 4
- 16566-89-C3 15% (15%L100) pH7.4 Flow8-1Tab – 5
- 16566-89-C3 15% (15%L100) pH7.4 Flow8-1Tab – 6

After drug release

Swelling polymer
+ enteric & seal coated API

Unswelled tablet          Swelled tablet

CONTROLLED RELEASE DOSAGE FORM FOR ONCE DAILY ADMINISTRATION OF DIMETHYL FUMARATE

CROSS-REFERENCE TO RELATED PATENT APPLICATIONS

This application is a national stage of International Patent Application No. PCT/US2014/070058, filed Dec. 12, 2014, which claims the benefit of U.S. Provisional Application No. 61/916,115, filed Dec. 13, 2013, which is incorporated by reference herein in its entirety.

FIELD OF INVENTION

The present invention generally relates to controlled release dosage form for once daily administration of dimethyl fumarate (DMF) and uses thereof.

BACKGROUND OF THE INVENTION

TECFIDERA™ has been approved by the U.S. Food and Drug Administration for the treatment of patients with relapsing forms of multiple sclerosis (MS). TECFIDERA™ contains dimethyl fumarate (DMF), which has the following structure:

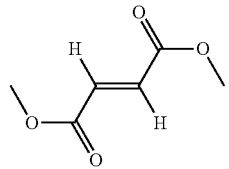

The starting dose for TECFIDERA™ is 120 mg twice a day orally. After 7 days, the dose is to be increased to the maintenance dose of 240 mg twice a day orally. TECFIDERA™ can be taken with or without food.

There is currently no FDA approved once a day dosing regimen, i.e., QD dosing, for DMF. One objective of the present invention is to develop a formulation (e.g., a unit dosage form) that is suitable for once a day dosing.

BRIEF SUMMARY OF THE INVENTION

In various embodiments, the invention provides a controlled release dosage form that releases MMF, a compound that can be metabolized into MMF in vivo (e.g., DMF), or a pharmaceutically acceptable salt thereof or combinations thereof (collectively "API"), in the gastrointestinal ("GI") tract of a subject in a sustained or pulsatile manner. In some embodiments, the API in the controlled release dosage form is retained in the stomach and/or small intestine of a subject treated for at least 3 hours (e.g., about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, or any ranges thereof). In some embodiments, the controlled release dosage form is a matrix dosage form, an osmotic dosage form, a gastric retention dosage form, an intestinal retention dosage form, or a combination thereof. In some embodiments, a daily amount of the API (e.g., 480 mg of DMF) is provided by one or more units of the controlled release dosage system alone. In some embodiments, the daily amount of the API is provided by one or more units of the controlled release dosage form in combination with one or more units of an enterically coated immediate release dosage form.

In some embodiments, the invention provides a matrix dosage form for delivering an API to a subject treated. In some aspects, the matrix dosage form releases the API in the GI tract of a subject in a sustained period of time from about 2 to about 24 hours (e.g., about 2, about 4, about 6, about 8, about 10, about 12, about 14, about 16, about 18, about 20, about 22, or about 24 hours). In some aspects, the matrix dosage form exhibits zero-order release of the API. In some embodiments, the matrix dosage form comprises a bilayer or monolithic tablet. In some aspects, the matrix dosage form comprises a plurality of microtablets. In some aspects, the bilayer or monolithic tablet or the microtablets are coated (e.g., enterically coated).

In some embodiments, the invention provides an osmotic dosage form for delivering an API to a subject treated. In some aspects, the osmotic dosage form releases the API in the GI tract of a subject in a sustained period of time from about 2 to about 24 hours (e.g., about 2, about 4, about 6, about 8, about 10, about 12, about 14, about 16, about 18, about 20, about 22, or about 24 hours). In some aspects, the osmotic dosage form comprises an osmotic monolithic tablet.

In some embodiments, the invention provides a gastric retention dosage form for delivering an API to a subject treated. In some aspects, the gastric retention dosage form releases the API in the GI tract of a subject (e.g. in the stomach or the small intestine) treated in a sustained period of time (e.g., about 2, about 4, about 6, about 8, about 10, about 12, about 14, about 16, about 20, or about 24 hours). In some aspects, the gastric retention dosage form, by itself or in combination with a second dosage form (enterically coated immediate release or delayed release), releases the API in the GI tract of a subject in a pulsatile manner with a lag time from about 2 hours to about 14 hours (e.g., about 2 hours, about 4 hours, about 6 hours, about 8 hours, about 10 hours, about 12 hours, about 14 hours, or any ranges thereof).

In some aspects, the gastric retention dosage form is retained in the stomach, for example, has a gastric retention time of from about 0.2 hour to about 18 hours (e.g., about 0.2 hour, about 0.5 hour, about 1 hour, about 2 hours, about 3 hours, about 4 hours, about 6 hours, about 8 hours, about 10 hours, about 12 hours, about 14 hours, about 16 hours, about 18 hours, or any ranges thereof).

In some aspects, the gastric retention dosage form is a floating dosage form. In some aspects, the floating dosage form is a floating tablet (e.g., a bilayer or a trilayer tablet) or a floating capsule. In some aspects, the floating dosage form is a sustained release dosage form. In some aspects, the floating dosage form is a delayed release dosage form, which when administered together with a second dosage form (e.g., an enterically coated immediate release dosage form, or a delayed release dosage form) provides a pulsatile release of the API with a lag time from about 2 hours to about 14 hours (e.g., about 2 hours, about 4 hours, about 6 hours, about 8 hours, about 10 hours, about 12 hours, about 14 hours, or any ranges thereof).

In some aspects, the gastric retention dosage form is a swelling dosage form. In some aspects, the swelling dosage form is a swelling tablet (e.g., a monolithic, bilayer, or trilayer tablet) or a swelling sheet. In some aspects, the swelling dosage form is a sustained release dosage form. In some aspects, the swelling dosage form is a delayed release dosage form, which when administered together with a second dosage form (e.g., an enterically coated immediate release dosage form, or a delayed release dosage form) provides a pulsatile release of the API with a lag time from about 2 hours to about 14 hours (e.g., about 2 hours, about 4 hours, about 6 hours, about 8 hours, about 10 hours, about 12 hours, about 14 hours, or any ranges thereof).

In some embodiments, the invention provides an intestinal retention dosage form for delivering an API to a subject treated. In some aspects, the intestinal retention dosage form releases the API in the GI tract of a subject in a sustained period of time (e.g., about 2, about 4, about 6, about 8, about 10, about 12, about 14, about 16, about 18, about 20, about 22, or about 24 hours). In some aspects, the intestinal retention dosage form comprises a mucoadhesive dosage form, which is adhesive to mucosal surface of the gastrointestinal tract (e.g., small intestine) of a subject treated. In some aspects, the intestinal retention dosage form comprises a dosage form comprising a plurality of particles having a mean diameter of about 50 microns to about 1000 microns (e.g., about 50, 100, 150, 200, 300, 400, 500, 750, 1,000 microns, or any ranges thereof) that are retained in the GI tract (e.g., small intestine) for an extended period of time from about 2 hours to about 12 hours (e.g., about 2, 3, 4, 5, 6, 7, 8, 10, 12, or any ranges thereof). In some aspects, the particles have a mean diameter of about 100 microns to about 500 microns.

In some embodiments, a daily amount of the API is provided by one or more units (e.g., 1, 2, 3, 4, or 5) of the controlled release dosage form described above (e.g., matrix dosage form, osmotic dosage form, gastric retention dosage form, or intestinal retention dosage form). In some embodiments, the daily amount of the API is provided by a single unit of the controlled release dosage form described above, i.e., one unit per day. In some embodiments, the daily amount of the API is provided by one or more units (e.g., 1, 2, 3, 4, or 5) of the controlled release dosage form described above and one or more units (e.g., 1, 2, 3, 4, or 5) of an enterically coated immediate release dosage form (e.g., as described herein).

Certain embodiments of the invention are directed to pulsatile delivery of an API to a subject treated. In some embodiments, the invention provides a system that delivers to the GI tract (e.g., upper GI tract or lower GI tract (e.g., the small intestine)) of a subject treated, more than one dose of the API, in a pulsatile manner.

Certain embodiments of the invention are directed to a pharmaceutical formulation, wherein the pharmaceutical formulation when orally dosed to a subject, delivers to the GI tract (e.g., upper GI tract or lower GI tract (e.g., the small intestine)) of the subject treated more than one dose of an API, in a pulsatile manner.

In some embodiments, the invention provides a unit dosage form. In some aspects, the unit dosage form is a single unit of one of the controlled release dosage forms described above (e.g., one unit of matrix dosage form, osmotic dosage form, gastric retention dosage form, or intestinal retention dosage form). In some aspects, the unit dosage form, which when orally dosed to a subject, delivers more than one dose of an API, wherein the unit dosage form comprises:

(a) a first dosage component comprising a first dose of the API; and (b) a second dosage component comprising a second dose of the API.

In some aspects, the second dosage component is one of the controlled release dosage forms described above. In another embodiment, the first dosage component is an enterically coated immediate release dosage form.

In some aspects, the pulsatile manner is characterized by a lag time of about 2 hours to about 14 hours (e.g., about 8 hours to about 12 hours) between delivery of the first and second doses of the API.

In some aspects, a subject orally administered a controlled release dosage form or an unit dosage form described above (with or without food) once daily exhibits one or more of the following pharmacokinetic parameters: (a) a mean plasma MMF $AUC_{overall}$ ranging from about 4.81 h·mg/L to about 11.2 h·mg/L; (b) a mean plasma MMF $AUC_{0-12}$ ranging from about 2.4 h·mg/L to about 5.5 h·mg/L; and (c) a mean $AUC_{0-infinity}$ ranging from about 2.4 h·mg/L to about 5.6 h·mg/L.

In some embodiments, the invention provides a method of treating a disease or disorder (e.g., multiple sclerosis) in a subject in need thereof, wherein the method comprises administering to the subject a controlled release dosage form or a unit dosage form described above once per day.

In some aspects, the controlled release dosage form comprises 80 mg to 1000 mg of an API (e.g., 480 mg API).

In some aspects, the unit dosage form comprises (a) a first dosage component comprising a first dose of about 80 mg to about 1000 mg (e.g., about 120 mg or about 240 mg) of an API; and (b) a second dosage component comprising a second dose of about 80 mg to about 1000 mg (e.g., about 120 mg or about 240 mg) of the API;

In some embodiments, the first and second dosage components are physically separated from each other (e.g., as two capsules, two tablets, or one capsule and one tablet) and are provided in a kit (e.g., a blister pack). In some embodiments, the first and second dosage components are both part of one dosage form (e.g., a pill, a tablet, or a capsule).

In some embodiments, the only active ingredient in the controlled release dosage form or unit dosage form described above is DMF.

BRIEF DESCRIPTION OF THE DRAWINGS/FIGURES

FIGS. 1A and 1B show a design of a delayed release tablet formulation. FIG. 1A shows a design of a coated delayed release minitablet/microtablet which contains a core tablet matrix, a seal coating layer, a semipermeable coating layer, and a pH7 release coating layer. FIG. 1B shows a picture and a microscopic view of a delayed release tablet prepared according to Example 1 with three coating layers: an inner seal coating layer, a semipermeable coating layer, and an outer pH 7 release coating layer.

Figure 4:
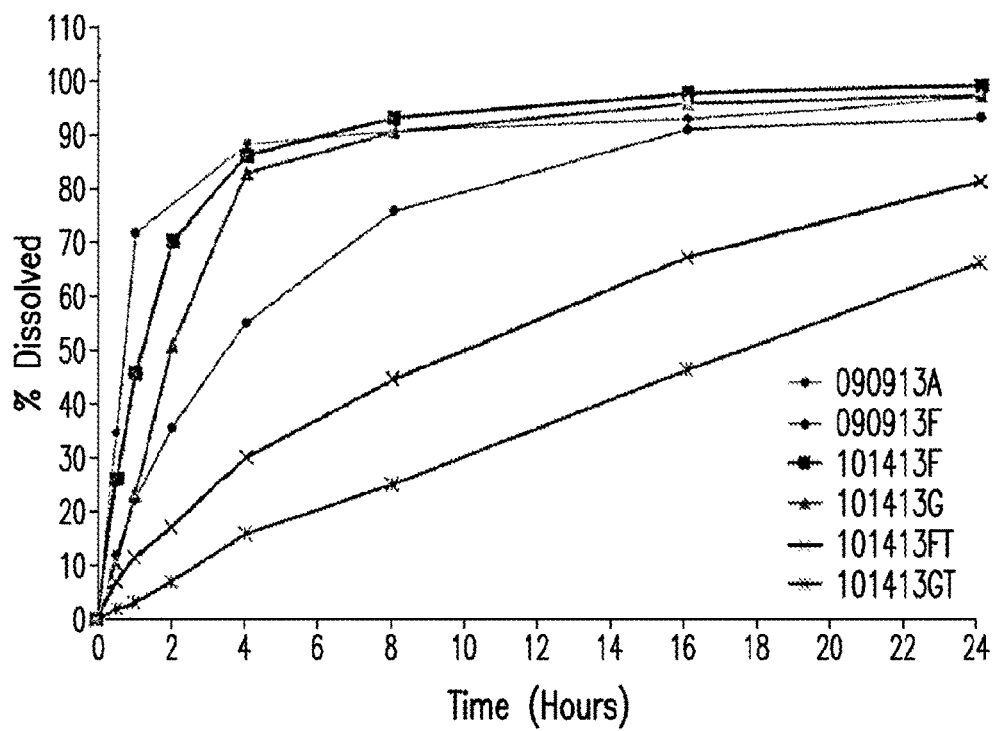

FIG. 4 shows in vitro dissolution profile of six different matrix formulations. Formulations 090913A, 090913F, 101413F and 101413G each contains a plurality of microtablets. Formulations 101413FT and 101413GT have the same ingredients as 101413F and 101413G, respectively, but are made as monolithic tablets. The dissolution tests were performed according to USP apparatus II (paddle) at an agitation speed of 75 rpm.

Figure 5:
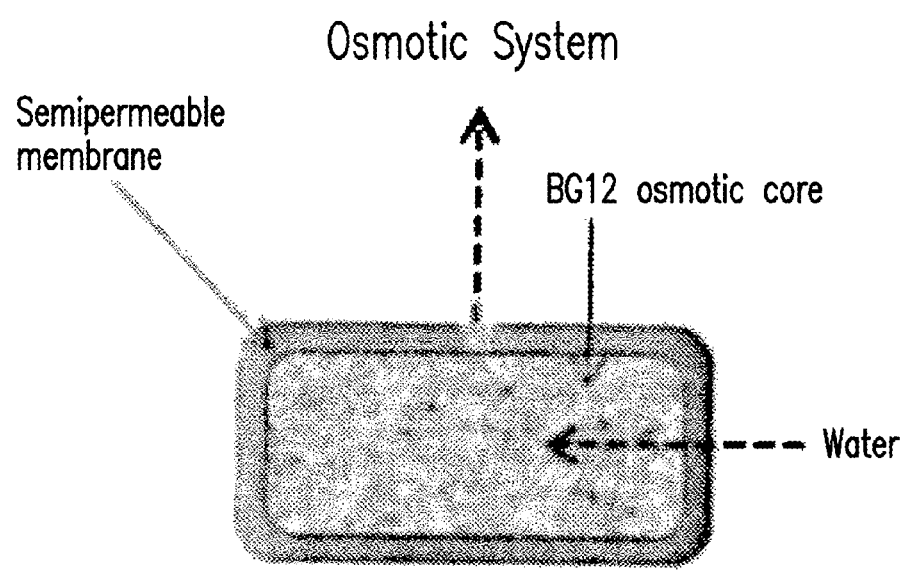

FIG. 5 shows a design of an osmotic dosage form which contains an osmotic core containing DMF and a semipermeable membrane coating encapsulating the core. The semipermeable membrane allows water into the tablet which creates osmotic pressure that forces the drug out of the coated tablet through a laser drilled hole in the coating. In this design, DMF may be released over a sustained period of time (e.g., about 6 hours).

Figure 6A:
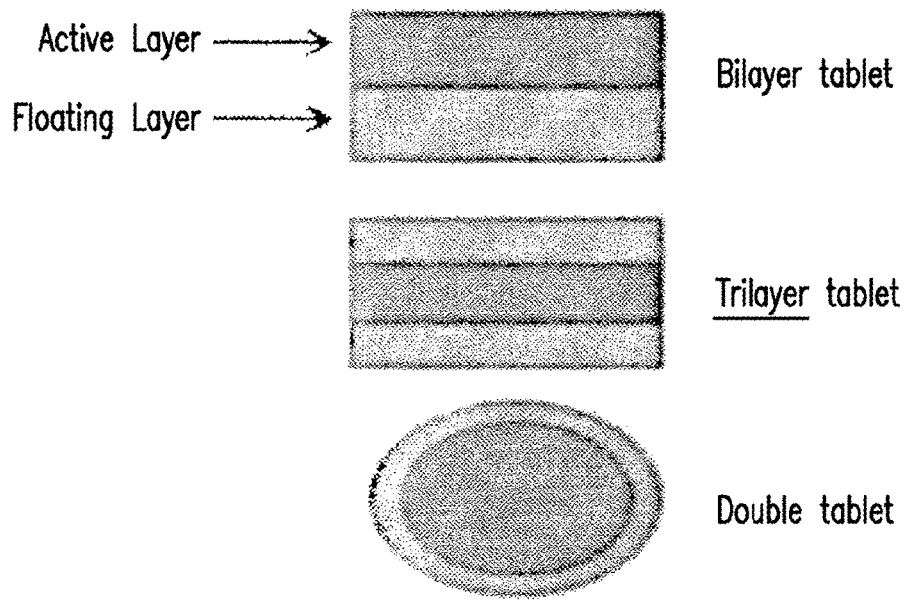
Figure 6B:
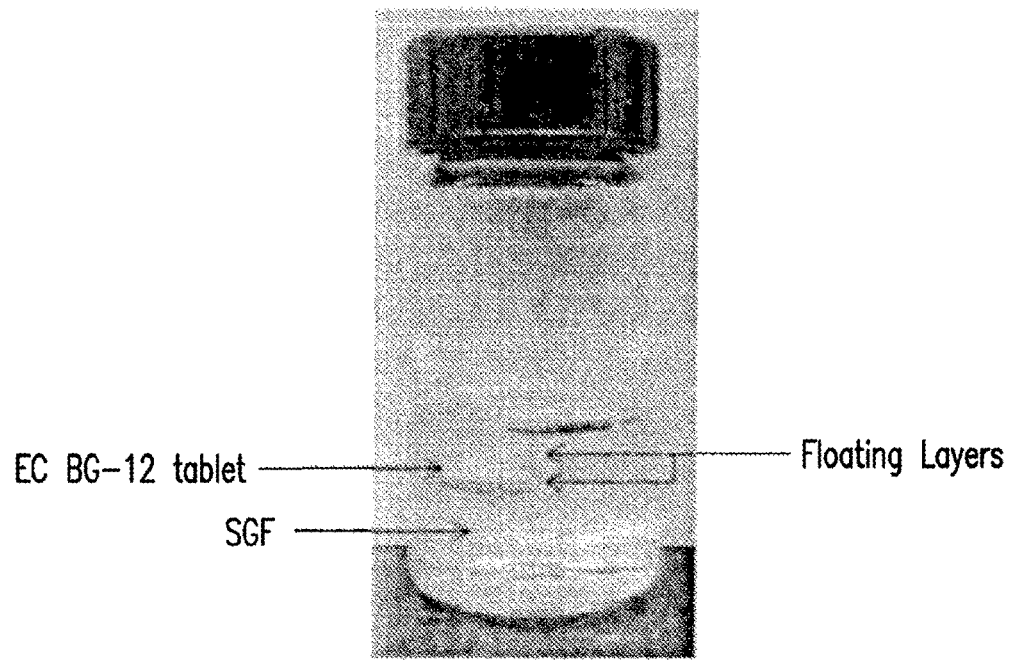

FIG. 6A shows three different designs of a floating dosage formulation: a bilayer, a trilayer, and a double tablet. Each design has an active layer, which contains DMF, and a floating layer. The bilayer design contains only one active layer and one floating layer. The trilayer design contains two floating layers and one active layer in between. The double tablet design has the floating layer encapsulating the active layer. FIG. 6B shows a picture of a trilayer floating tablet, which contains two effervescent floating layer with one enterically coated active layer containing DMF, floating in simulated gastric fluid.

Figure 7A:
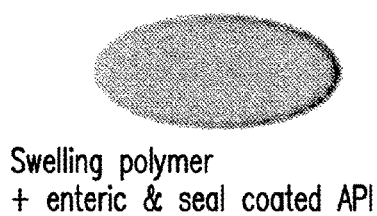
Figure 7B:
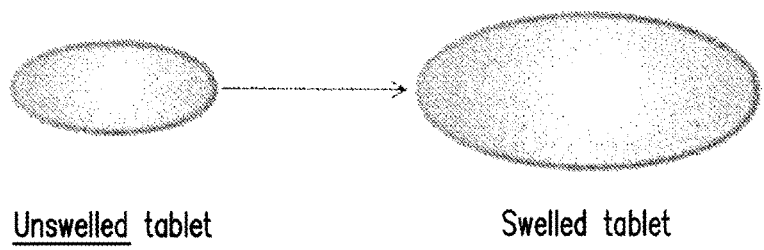
Figure 7C:
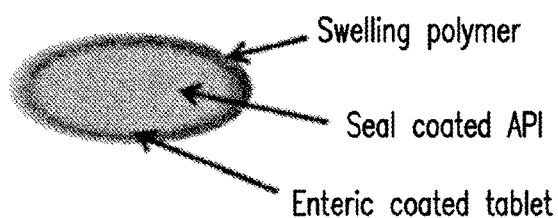
Figure 7D:
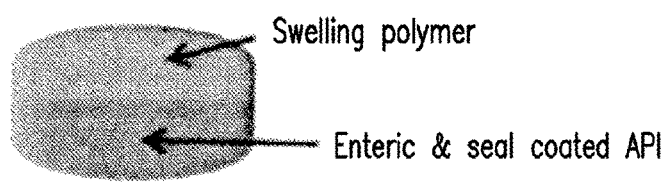

FIG. 7A shows a design of swellable tablet formulation for sustained release. The swellable tablet contains an API (e.g., DMF) that is seal coated and enterically coated and one or more swelling polymers. FIG. 7B shows that the swellable tablet can expand significantly which allows the swelled tablet to be retained in the stomach of a subject treated. FIG. 7C shows a design of swellable tablet formulation for delayed release. The swellable tablet contains a core containing an API (e.g., DMF) that is seal coated and enterically coated and one or more swelling polymers encapsulating the core. FIG. 7D shows another design of swellable tablet formulation for delayed release. The swellable tablet contains two layers: an active layer containing an API (e.g., DMF) that is seal coated and enterically coated and a swelling layer containing one or more swelling polymers. The two layers are joined together to form a bilayer tablet structure.

DETAILED DESCRIPTION OF THE INVENTION

Definitions

As used herein, "a" or "an" means one or more unless otherwise specified.

Unless specifically stated or obvious from context, as used herein, the term "about" is understood as within a range of normal tolerance in the art, for example, within 20% of the stated value. As used herein, "about" a specific value also includes the specific value, for example, about 10% includes 10%.

As used herein, the term "DMF," "BG-12," or "BG00012" refers to the compound dimethyl fumarate. And the term "MMF" refers to the compound, or an ionized form of monomethyl fumarate. A compound that can be metabolized into MMF in vivo, as used herein, includes DMF. A compound that can be metabolized into MMF in vivo, as used herein also includes, for example, any compound described in U.S. application Ser. No. 13/760,916, the content of which is incorporated herein by reference in its entirety.

As used herein, the abbreviation API refers to MMF, a compound that can be metabolized into MMF in vivo (e.g., DMF), or a pharmaceutically acceptable salt thereof or combinations thereof. In some embodiments, the API can include more than one compound, for example, a combination of MMF and DMF. In some embodiments, the API is a single compound, e.g., DMF.

Open terms such as "include," "including," "contain," "containing" and the like mean "comprising."

The term "treating" refers to administering a therapy in an amount, manner, or mode effective to improve a condition, symptom, or parameter associated with a disease or disorder.

The term "prophylaxis" or the term "prophylactic treatment" refers to preventing a disorder or preventing progression of a disorder, to either a statistically significant degree or to a degree detectable to one skilled in the art.

As used herein, a controlled release dosage form may be any dosage form that is capable of releasing a drug in a body over an extended period of time. The controlled release dosage form herein includes, without limiting to, sustained release dosage form, delayed release dosage form, and pulsatile release dosage form. In some embodiments, the controlled release dosage form herein is gastric retentive, which is retained in the stomach for a period (i.e., the gastric retention time) that is longer than the normal emptying time from the stomach, e.g., longer than about 0.2 hours, following an average meal. In any of the embodiments described herein, the gastric retention time of a gastric retentive controlled release dosage form may be about 0.2 hours to about 18 hours. In some embodiments, a gastric retentive controlled release dosage form is retained in the stomach for about 0.2 hour, about 0.5 hour, about 1 hour, about 2 hours, about 3 hours, about 4 hours, about 6 hours, about 8 hours, about 10 hours, about 12 hours, about 14 hours, about 16 hours, about 18 hours, or any ranges thereof.

The term "microtablet" means a compact in the form of a small (micro) tablet having a mean diameter of less than 5,000 microns (e.g., about 1,000 microns to about 3,000 microns), excluding any coating, that comprises the active ingredient(s) and one or more excipients. The active ingredient(s) and excipients can be homogeneously or heterogeneously mixed in the microtablet. In any of the embodiments described herein, the microtablets may be coated, for example, by a seal coating, an enteric coating, or a combination thereof.

As used herein, when an object (e.g., a first or second dosage component, drug product layer, etc.) is said to be "coated" or have a "coating," it is to be understood that the object can be fully or partially coated by one or more coatings. Similarly, when an object (e.g., a first or second dosage component, drug product layer, etc.) is said to be "encapsulated." it is to be understood that the object can be fully or partially encapsulated.

Delivering a drug (e.g., DMF) in a pulsatile manner or in pulses may be understood as involving rapid and transient release of a dose of the drug (e.g., DMF) within a short time period immediately after a lag time.

The term "lag time" as used herein refers to the time between the time of the beginning of delivery of a drug (e.g., DMF) from one component and the subsequent beginning of delivery of the drug (e.g., DMF) from another component. For example, the lag time may refer to the time between the beginning of delivery of the first and second doses of an API upon administering a unit dosage form (e.g., as described herein).

As used herein, a pre-determined lag time of a pulsatile dosage form refers to the lag time that may be determined by in vitro dissolution experiments. For example, for a pulse dosage form containing only one dose of a drug (e.g., DMF), a pre-determined lag time may refer to the time duration between the time when the dosage form is in contact with a gastric liquid or simulations thereof (i.e., the time around when an immediate release dosage form would release the drug) and the time when substantially all of the drug (e.g., DMF) is released from the gastro-retentive dosage form. Alternatively, for dosage forms that contain more than one dose of a drug (e.g., DMF), the pre-determined lag time may refer to the time between releases of any two consecutive doses as determined by in vitro dissolution experiments. The pre-determined lag time herein may be from about 2 hours to about 14 hours. In some embodiments, the pre-determined lag time is about 2 hours, about 4 hours, about 6 hours, about 8 hours, about 10 hours, about 12 hours, about 14 hours, or any ranges thereof. In some embodiments, the pre-determined lag time is about 8 hours to about 12 hours. A pre-determined lag time may be controlled via various techniques. For example, by varying polymer components and/or thickness of lag time control coatings or layers (e.g., pulsatile coatings described herein) in the controlled release dosage forms, different pre-determined lag times can be achieved.

The term "subject" as used herein generally refers to human, including healthy human or a patient with certain diseases or disorders.

Controlled Release Dosage Form

In various embodiments, the invention provides a controlled release dosage form that release an API in the GI tract of a subject in a sustained or pulsatile manner. In some embodiments, the API in the controlled release dosage form is retained in the stomach and/or small intestine of a subject treated for at least 3 hours (e.g., about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, or any ranges thereof). In some embodiments, the API in the controlled release dosage form is retained in the stomach and/or small intestine for about 3 hours to about 17 hours. In some embodiments, the API in the controlled release dosage form is retained in the stomach and/or small intestine of a subject treated for at least 4 hours, at least 5 hours, at least 6 hours, at least 7 hours, or at least 8 hours. In some embodiments, the API in the controlled release dosage form is retained in the stomach and/or small intestine of a subject treated for at least 5 hours, at least 6 hours, or at least 7 hours.

The controlled release dosage form can be a matrix dosage form, an osmotic dosage form, a gastric retention dosage form, an intestinal retention dosage form, or a combination thereof.

In some embodiments, a subject administered one or more units (e.g., 1, 2, 3, 4, 5, or 6) of the controlled release dosage form (with or without food) once daily produces one or more of the following pharmacokinetic parameters in the subject: (a) a mean plasma MMF $AUC_{overall}$ ranging from about 4.81 h·mg/L to about 11.2 h·mg/L; (b) a mean plasma MMF $AUC_{0-12}$ ranging from about 2.4 h·mg/L to about 5.5 h·mg/L; and (c) a mean $AUC_{0\text{-}infinity}$ ranging from about 2.4 h·mg/L to about 5.6 h·mg/L. In some embodiments, the subject treated exhibits a pharmacokinetic profile characterized by both (a) and (b), both (a) and (c), or both (b) and (c). In some embodiments, the subject treated exhibits a pharmacokinetic profile characterized by (a), (b), and (c).

In some embodiments, a subject orally administered a single unit of the controlled release dosage form (with or without food) or a unit dosage form described herein once daily produces one or more of the following pharmacokinetic parameters in the subject: (a) a mean plasma MMF $AUC_{overall}$ ranging from about 4.81 h·mg/L to about 11.2 h·mg/L; (b) a mean plasma MMF $AUC_{0-12}$ ranging from about 2.4 h·mg/L to about 5.5 h·mg/L; and (c) a mean $AUC_{0\text{-}infinity}$ ranging from about 2.4 h·mg/L to about 5.6 h·mg/L. In some embodiments, the subject treated exhibits a pharmacokinetic profile characterized by both (a) and (b), both (a) and (c), or both (b) and (c). In some embodiments, the subject treated exhibits a pharmacokinetic profile characterized by (a), (b), and (c).

In some embodiments, a subject orally administered a single unit of the controlled release dosage form or a unit dosage form described herein (with or without food) once daily exhibits a mean MMF plasma area under the curve 0-12 ($AUC_{0-12}$) of about 2.36 h·mg/L to about 5.50 h·mg/L, from about 2.75 h·mg/L to about 5.10 h·mg/L, or from about 3.14 h·mg/L to about 4.91 h·mg/L. In one embodiment, the subject exhibits a mean $AUC_{0-12}$ of about 3.93 h·mg/L.

In some embodiments, a subject orally administered a single unit of the controlled release dosage form or a unit dosage form described herein (with or without food) once daily exhibits a mean MMF plasma overall area under the curve ($AUC_{overall}$) of about 4.81 h·mg/mL to about 11.2 h·mg/mL, or from about 6.40 h·mg/L to about 10.1 h·mg/L. In one embodiment, the subject exhibits a mean $AUC_{overall}$ of about 8.02 h·mg/L.

In some embodiments, suitable amounts of API for the controlled release dosage form include those that can provide, by itself or in combination with one or more doses from, for example, a second dosage form (e.g., a controlled release dosage form or an enterically coated immediate release dosage form), a daily amount of the respective compound (e.g., DMF) ranging from about 1 mg/kg to about 50 mg/kg (e.g., from about 2.5 mg/kg to about 20 mg/kg or from about 2.5 mg/kg to about 15 mg/kg).

The controlled release dosage form contains any therapeutically effective dose of an API, e.g., an amount that is effective in treating multiple sclerosis. For example, suitable doses of DMF in the controlled release dosage form may be any dose from about 20 mg to about 1 g of DMF. In some embodiments, the suitable doses of DMF in the controlled release dosage form may be any dose from about 80 mg to about 1000 mg of DMF. In some embodiments, the suitable doses of DMF in the controlled release dosage form may be any dose from about 100 mg to about 750 mg of DMF. In some embodiments, the suitable doses of DMF in the controlled release dosage form is about 200 to about 600 mg. In some embodiments, the suitable doses of DMF in the controlled release dosage form may be any dose from about 300 to about 600 mg. In some embodiments, the suitable doses of DMF in the controlled release dosage form is about 480 mg.

In some embodiments, the DMF in the controlled release dosage form is about 60 mg, about 80 mg, about 100 mg, about 120 mg, about 160 mg, about 200 mg, about 240 mg, about 320 mg, about 360 mg, about 400 mg, about 480 mg, about 600 mg, about 720 mg, about 800 mg, about 900 mg, about 1000 mg of DMF, or any ranges thereof.

The controlled release dosage form can contain an amount of a compound that that can metabolize into MMF that provides an equivalent amount of MMF as the doses of DMF described above.

In some embodiments, the daily amount of the API is provided by one or more units (e.g., 1, 2, 3, 4, or 5) of the controlled release dosage form herein. In some embodiments, the daily amount of the API is provided by a single unit of the controlled release dosage form herein, i.e., one unit per day. In some embodiments, one or more units (e.g., 1, 2, 3, 4, or 5) of the controlled release dosage form herein is co-administered with one or more units (e.g., 1, 2, 3, 4, or 5) of a second dosage form (e.g., as described herein) to provide the daily amount of the API to a subject. In some embodiments, the daily amount of the API is provided by one or more units (e.g., 1, 2, 3, 4, or 5) of the controlled release dosage form described herein and one or more units (e.g., 1, 2, 3, 4, or 5) of an enterically coated immediate release dosage form (e.g., as described herein). For example, in some embodiments, two units of the controlled release dosage form (e.g., two of the osmotic dosage form described herein) and one enterically coated immediate release dosage form is combined, for example, in a capsule, or a tablet, to provide the daily amount of the API (e.g., DMF) to a subject.

In some embodiments, the controlled release dosage form comprises an acid soluble outer coating. Suitable acid soluble coatings for the first dosage component are known in the art and include those coatings that dissolve at a pH less than 6.0. Non-limiting examples of acid soluble coatings include gelatin, Eudragit® E-100, polyvinyl acetyl diethyl-aminoacetate, and chitosan coatings. The acid-soluble coating may be applied using various techniques (e.g., spray techniques) known to one skilled in the art.

In addition to the components listed below for each controlled release dosage form, the controlled release dosage form may also comprise one or more pharmaceutically acceptable excipients in addition to those described above. Suitable pharmaceutically acceptable excipients are those known in the art, for example, binders, fillers, disintegrants, glidants, lubricants, diluents, plasticizers, etc. as described in Remington's Pharmaceutical Science, 18$^{th}$ Edition, 1990, Mack Publishing Company, Easton, Pa. ("Remington's").

Matrix Dosage Form

In some embodiments, the invention provides a matrix dosage form for delivering an API to a subject treated. The matrix dosage form herein comprises a core comprising an API, one or more release modifying polymers, and one or more pharmaceutically acceptable excipients. Suitable release modifying polymers for a matrix dosage form include cellulose and cellulose derivatives, such as microcrystalline cellulose, hydroxypropyl methyl cellulose, hydroxypropyl cellulose and methylcellulose, Eudragit polymers (e.g., Eudragit RS, RL), povidone, polyvinyl acetate, poly(ethyleneoxide) (PEO), polyethylene glycol (PEG), poly (vinyl alcohol) (PVA), xanthan gum, carrageenan and other synthetic materials. The amount of the release modifying polymers can be from about 2% to about 50% by weight of the matrix dosage form. In some embodiments, the amount of the release modifying polymers can be about 2%, about 5%, about 10%, about 15%, about 20%, about 25%, about 30%, about 35%, about 40%, about 45%, about 50%, or any ranges thereof, by weight of the matrix dosage form. Various techniques for preparing a matrix dosage form are known.

The matrix dosage form herein may also be coated. In some embodiments, the matrix dosage form comprises a seal coating encapsulating the core. In some embodiments, the matrix dosage form comprises an outer enteric coating. In some embodiments, the outer enteric coating encapsulates a seal coating. Various techniques for coating are known.

In some embodiments, the matrix dosage form exhibits zero-order release of the API. In some embodiments, the matrix dosage form releases the API in the GI tract of a subject in a sustained period of time from about 2 to about 24 hours (e.g., about 2, about 4, about 6, about 8, about 10, about 12, about 14, about 16, about 18, about 20, about 22, about 24 hours, or any ranges thereof). In some embodiments, the matrix dosage form releases the API in the GI tract of a subject in about 2 to about 10 hours. In some embodiments, the matrix dosage form releases the API in the GI tract of a subject in about 4 to about 6 hours. In some embodiments, the API is released in the stomach. In some embodiments, the API is released in the upper GI tract. In some embodiments, the API is released in the lower GI tract. In some embodiments, the API is released in the small intestine.

The rate of release can be modified by varying the amount, type, and ratio of the one or more release modifying polymers.

The rate of release can also depend on the form (e.g., tablet or microtablets) of the matrix dosage form. In some embodiments, the matrix dosage form comprising the API is a bilayer or monolithic tablet. In some embodiments, the matrix dosage form comprises a plurality of microtablets comprising the API. In some embodiments, the bilayer or monolithic tablet, or the microtablets are coated (e.g., enterically coated).

The release profile of the matrix dosage form herein can be determined by an in vitro dissolution method. Standard test protocols for in vitro dissolution are known. In some embodiments, the release profile of the matrix dosage form is characterized in that more than about 80% of the API is released in less than about 8 hours (e.g., about 6 hours, about 4 hours), when tested by United State Pharmacopoeia (USP) Dissolution Apparatus 2 according to standardized and specified in USP General Chapter <711> Dissolution, at an agitation speed of 75 rpm. In some embodiments, the release profile of the matrix dosage form is characterized in that more than about 80% of the API is released in less than about 8 hours (e.g., about 6 hours, about 4 hours), when tested by United State Pharmacopoeia (USP) Dissolution Apparatus 2 according to standardized and specified in USP General Chapter <711> Dissolution, at an agitation speed of 100 rpm.

Osmotic Dosage Form

In any of the embodiments described herein, the controlled release dosage form is an osmotic dosage form. Various techniques for preparing an osmotic dosage form that include, but are not limited to monolithic tablets, bilayer tablets, and trilayer tablets, are known.

An osmotic dosage form can be a tablet with a semi-permeable membrane. The semi-permeable membrane allows water into the tablet which dissolves an osmotic agent that creates osmotic pressure and/or a hydrophilic polymer that suspends and carries the drug out of the coated tablet through a laser drilled hole in the coating.

The osmotic dosage form herein can include an osmotic core comprising an API, one or more osmotic agents, one or more pharmaceutically acceptable excipients, and optionally one or more release modifying polymers. In some embodiments, the semi-permeable membrane coated tablets could be encapsulated in a gelatin capsule. Suitable material for the semi-permeable membrane coatings includes those known in the art, for example, cellulose products such as cellulose acetate, ethyl cellulose, hydroxyalkyl cellulose (e.g., hydroxypropyl cellulose, hydroxypropyl methyl cellulose, hydroxyethyl cellulose). Suitable osmotic agents include those known in the art, for example, a sugar such as sorbitol, mannitol, xylitol, fructose or salts (e.g. sodium chloride). In some embodiments, the osmotic agents can be in an amount of about 10%, about 20%, about 30%, about 40%, about 50%, about 60%, or any ranges thereof, by weight of total weight of the osmotic dosage form. In some embodiments, the semi-permeable membrane coatings can be in an amount of about 2% to about 20% (e.g., about 2%, about 5%, about 10%, about 15%, about 20%, or any ranges thereof) by weight of total weight of the osmotic dosage form.

Other suitable material for the osmotic dosage form include those known in the art, for example, the osmotic dosage form may comprise a water swellable polymer (e.g. polyethylene oxide), a water soluble polymer, a water insoluble polymer (e.g. sodium carboxyl methyl cellulose), a water insoluble and water swellable polymer, a water insoluble and water permeable polymer, or combinations thereof.

In some embodiments, the osmotic dosage form comprises a polymer selected from the group consisting of homopolymer of N-vinyl pyrrolidone, copolymer of N-vinyl pyrrolidone, copolymer of N-vinyl pyrrolidone and vinyl acetate, copolymer of N-vinyl pyrrolidone and vinyl propionate, methylcellulose, ethylcellulose, hydroxyalkylcelluloses, hydroxypropylcellulose, hydroxyalkylalkylcellulose, hydroxypropylmethylcellulose, cellulose phthalate, cellulose succinate, cellulose acetate phthalate, hydroxypropylmethylcellulose phthalate, hydroxypropylmethylcellulose succinate, hydroxypropylmethylcellulose acetate succinate, polyethylene oxide, polypropylene oxide, copolymer of ethylene oxide and propylene oxide, methacrylic acid/ethyl acrylate copolymer, methacrylic acid/methyl methacrylate copolymer, butyl methacrylate/2-dimethylaminoethyl methacrylate copolymer, poly(hydroxyalkyl acrylate), poly(hydroxyalkyl methacrylate), copolymer of vinyl acetate and crotonic acid, partially hydrolyzed polyvinyl acetate, carrageenan, galactomannan or xanthan gum polyethylene oxide, and hydroxypropyl methylcellulose.

In some embodiments, the osmotic dosage form comprises a polymer selected from the group consisting of hydroxypropylcellulose, cross-linked polyvinylpyrrolidone, cross-linked carboxymethylcellulose, pregelatinized starch, sodium starch glycolate, polyvinyl acetate, polyacrylic acid, acrylate-co-polymer, carboxymethylcellulose calcium, carboxymethylcellulose sodium, poly(hydroxyethyl-methacrylate), poly(methacrylic acid), poly(acrylamide), sodium starch glycolate, starch, poly(hydroxyalkyl methacrylate) with a molecular weight of 32,000 to 5,500,000, poly(electrolyte) complexes, poly(vinyl alcohol), acrylate polymers with water absorbability of roughly 400 times its original weight, a mixture of poly(vinyl alcohol) and poly(N-vinyl-2-pyrrolidone), poly(acrylic acid) with a molecular weight of 80,000 to 200,000, polyoxy polyethylene oxide polymers with a molecular weight of 100,000 to 5,000,000, polysaccharides, agar, acacia, karaya, tragacanth and algins, pectin with a molecular weight of 30,000 to 300,000, and polyoxybutylenepolyethylene block polymer.

In some embodiments, the osmotic dosage form comprises a polymer selected from the group consisting of cellulose acylate, cellulose acetate, cellulose diacylate, cellulose diacetate, cellulose triacylate, cellulose triacetate, mono-, di-, and tri-cellulose alkenylate, mono-, di- and tri-alkenylates, mono-, di- and tri-aroylates, cellulose trivalerate, cellulose trilaurate, cellulose tripalmitate, cellulose trioctanoate, cellulose tripropionate, cellulose diesters, cellulose disuccinate, cellulose dipalmitate, cellulose dioctanoate, cellulose dicaprylate, cellulose acetate heptonate, cellulose valerate palmitate, cellulose acetate octonoate, cellulose propionate succinate, cellulose acetate valerate, cellulose acetaldehyde, dimethyl cellulose acetate, cellulose acetate ethylcarbamate, hydroxypropylmethylcellulose, semipermeable polyamylsulfanes, semipermeable urethane, cellulose acetate methylcarbamate, cellulose dimethylaminoacetate, semipermeable sulfonated polystyrenes, semipermeable silicone rubbers, semipermeable styrenes, sulfonated polystyrenes, polyurethanes, polydiethylaminomethylstyrene, cellulose acetate methylcarbamate, ethylcellulose, shellac, polymethylstyrene, polyvinylacetate, semipermeable (polysodium styrenesulfonate), and semipermeable poly(vinylbenzymtrimethylammonium chloride.

In some embodiments, the osmotic dosage form comprises a polyethylene oxide or hydroxypropyl methylcellulose. Various commercially available polyethylene oxide (e.g., Polyox N-80, WSR N-750 or WSR-205) and hydroxypropyl methylcellulose (e.g., Methocel K100 Premium LV or E50 Premium LV) are suitable for use in the osmotic dosage form.

In some embodiments, the osmotic dosage form releases the API and exhibits zero-order release of the API. In some embodiments, the osmotic dosage form releases the API in the GI tract of a subject in a sustained period of time from about 2 to about 24 hours (e.g., about 2, about 4, about 6, about 8, about 10, about 12, about 14, about 16, about 18, about 20, about 22, about 24 hours, or any ranges thereof). In some embodiments, the osmotic dosage form releases the API in the GI tract of a subject in about 2 to about 10 hours. In some embodiments, the osmotic dosage form releases the API in the GI tract of a subject in about 4 to about 6 hours. In some embodiments, the API is released in the stomach. In some embodiments, the API is released in the upper GI tract. In some embodiments, the API is released in the lower GI tract. In some embodiments, the API is released in the small intestine.

The release profile of the osmotic dosage form herein can also be determined by an in vitro dissolution method. Standard test protocols for in vitro dissolution are known. In some embodiments, the release profile of the osmotic dosage form is characterized in that more than about 80% of the API is released in less than about 8 hours (e.g., about 6 hours, about 4 hours), when tested by USP Dissolution Apparatus 2 according to standardized and specified in USP General Chapter <711> Dissolution, at 75 rpm. In some embodiments, the release profile of the matrix dosage form is characterized in that more than about 80% of the API is released in less than about 8 hours (e.g., about 6 hours, about 4 hours), when tested by USP Dissolution Apparatus 2 according to standardized and specified procedures in USP General Chapter <711> Dissolution, at 100 rpm.

Gastric Retention Dosage Form

In some embodiments, the invention provides a gastric retention dosage form for delivering an API to a subject treated. In some embodiments, the gastric retention dosage form releases the API in the GI tract of a subject in a sustained period of time (e.g., about 2, about 4, about 6, about 8, about 10, about 12, about 14, about 16, about 18, about 20, about 22, or about 24 hours). In some embodiments, the gastric retention dosage form releases the API in the GI tract of a subject in a pulsatile manner with a lag time from about 2 hours to about 14 hours (e.g., about 2 hours, about 4 hours, about 6 hours, about 8 hours, about 10 hours, about 12 hours, about 14 hours, or any ranges thereof).

In some embodiments, the gastric retention dosage form is retained in the stomach of a subject treated, for example, has a gastric retention time of from about 0.2 hour to about 18 hours (e.g., about 0.2 hour, about 0.5 hour, about 1 hour, about 2 hours, about 3 hours, about 4 hours, about 6 hours, about 8 hours, about 10 hours, about 12 hours, about 14 hours, about 16 hours, about 18 hours, or any ranges thereof). In some embodiments, the API in the gastric retention dosage form is retained in the stomach of a subject treated, for example, for about 0.2 hour to about 18 hours (e.g., about 0.2 hour, about 0.5 hour, about 1 hour, about 2 hours, about 3 hours, about 4 hours, about 6 hours, about 8 hours, about 10 hours, about 12 hours, about 14 hours, about 16 hours, about 18 hours, or any ranges thereof). In some embodiments, the API in the gastric retention dosage form is retained in the stomach of a subject treated for at least 3 hours (e.g., about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, or any ranges thereof). In some embodiments, the API in the gastric retention dosage form is retained in the stomach of a subject treated for about 3 hours to about 17 hours. In some embodiments, the API in the gastric retention dosage form is retained in the stomach of a subject treated for at least 4 hours, at least 5 hours, at least 6 hours, at least 7 hours, or at least 8 hours. In some embodiments, the API in the gastric retention dosage form is retained in the stomach of a subject treated for at least 5 hours, at least 6 hours, or at least 7 hours. Various means to achieve gastric retention are known. For example, in some embodiments, the gastric retention dosage form is a floating dosage form or a swelling dosage form.

Floating Dosage Form

In some embodiments, the controlled release dosage form is a floating dosage form that floats when exposed to gastric fluid and thereby retaining the API in the stomach of a subject treated. Various techniques for preparing a floating dosage form are known. In some embodiments, the floating dosage form is a floating tablet (e.g., a bilayer or a trilayer tablet) or a floating capsule.

The floating dosage form described herein can include an active layer and a floating layer, wherein the active layer comprises an API and one or more release modifying polymers. In some embodiments, the gastric retention time of the floating dosage form is from about 0.2 hour to about 18 hours (e.g., about 0.2 hour, about 0.5 hour, about 1 hour, about 2 hours, about 3 hours, about 4 hours, about 6 hours, about 8 hours, about 10 hours, about 12 hours, about 14 hours, about 16 hours, about 18 hours, or any ranges thereof). In some embodiments, the floating dosage form floats in the stomach until the active layer releases all the API. In some embodiments, the floating dosage form floats in the stomach before the active layer releases all the API. The gastric retention time of the floating dosage form can be controlled by adjusting the floating layer, for example, by adjusting the amount of gas that can be generated and the speed of gas generation. Other techniques for adjusting the gastric retention time are known.

Materials suitable for the floating layer include pharmaceutical excipients that can lower the density of the pharmaceutical composition. In some embodiments, the floating layer comprises one or more low density excipients selected from the group consisting of hydroxypropyl methylcellulose, hydrogenated castor oil, carboxymethylcellulose, ethylcellulose, cross-linked povidone, chitosan and combinations thereof. In some embodiments, the weight ratio for the one or more low density excipients are adjusted such that the density of the floating dosage form is lower than the density of the gastric fluid in a subject.

In some embodiments, the floating layer comprises a porous mineral material, such as calcium silicate. In some embodiments, the porous mineral material having air entrapped within are coated with a polymer (e.g., hydroxypropylcellulose or ethylcellulose) such that the air within the porous mineral material is retained. In some embodiments, the floating layer comprises a porous mineral material that further comprises one or more low density excipients as described herein.

In some embodiments, the floating layer comprises hollow microspheres or polycarbonate resin that floats in a gastric fluid of a subject.

In some embodiments, the floating layer comprises a gas-generating system. Suitable gas-generating systems are known in the art. In some embodiments, the floating layer comprises at least one gas-generating system (e.g., a carbon-dioxide generating system, e.g., comprises an alkali or alkaline earth metal carbonate or bicarbonate) and at least one hydrophilic polymer (e.g., polysaccharide substances, protein substances, poloxamers, high molecular weight polyethylene glycols, polymers of methacrylic acids, polymers of acrylic acids, derivatives of methacrylic acid, or derivatives of acrylic acid), a cellulose polymer such as hydroxyalkyl alkylcellulose (e.g., hydroxypropyl methylcellulose), or a porous mineral compound (e.g., a silica or silica derivative). In some embodiments, the floating layer comprises sodium carbonate and Methocel K100M. In some embodiments, the weight ratio of sodium carbonate to Methocel K100M is from about 1:50 to about 50:1 (e.g., about 1:1 to about 1:10, about 1:2 to about 1:5, or about 1:3). In some embodiment, the floating layer comprises an effervescent couple, wherein upon oral administration of the controlled release dosage form to a subject, the effervescent couple in the floating dosage form generates gas and causes the gastric retention dosage form to float in the gastric liquid of the subject.

The floating dosage form described herein can take various forms. For example, in some embodiments, the floating dosage form is a bilayer or a trilayer tablet, wherein the floating layer and the active layer are compressed or otherwise joined to form a tablet structure. In some embodiments, the floating dosage form is a double tablet structure, wherein the floating layer encapsulates the active layer. In some embodiments, the floating dosage form is a capsule (e.g., a soft gel or hard gel capsule) encapsulating the floating layer and the active layer. In some embodiments, the capsule is partially coated with acid insoluble polymer.

The floating dosage form described herein can be a sustained release dosage form or a delayed release dosage form depending on the configuration of the active layer.

In some embodiments, the floating dosage form can be a sustained release dosage form. For example, in some embodiments, the active layer is a matrix dosage form described herein or an osmotic dosage form described herein.

The floating dosage form can also be a delayed release dosage form. For example, in some embodiments, the active layer is a delayed release dosage form, which, when administered together with a second dosage form (e.g., an enterically coated immediate release dosage form, or a delayed release dosage form), provides a pulsatile release of the API with a lag time from about 2 hours to about 14 hours (e.g., about 2 hours, about 4 hours, about 6 hours, about 8 hours, about 10 hours, about 12 hours, about 14 hours, or any ranges thereof). Suitable methods for preparing a delayed release dosage form comprising an API (e.g., coated API) include those known. In some embodiments, the delayed release dosage form may contain an enterically coated active layer and/or an enterically coated API. In some embodiments, the delayed release dosage form comprises about 90% by weight of a coated API (e.g., coated DMF particles) and about 10% by weight of a cellulose polymer (e.g., hydroxypropyl methylcellulose, Methocel E3 LV). In some embodiments, the delayed release dosage form may contain a core comprising an API, an inner seal coating, followed by a semipermeable coating. In some embodiments, the delayed release dosage form may further comprise an outer enteric coating. See examples in Example 1.

More than one active layers and/or more than one floating layers can also be included in the floating dosage form described herein. In some embodiments, the floating dosage form comprises two floating layers. In some embodiments, the active layer is placed between the two floating layers. In any of the embodiments described herein, wherein the floating dosage form comprises three layers (e.g., two active layers one floating layer, or two floating layers one active layer), the floating dosage form may be a trilayer tablet or a capsule encompassing the three layers.

In some embodiments, the floating dosage form comprises a second active layer. In some embodiments, the second active layer is an enterically coated immediate release dosage component, provided that the enterically coated immediate release dosage component is not placed between the active layer and the floating layer in a trilayer tablet structure. In some embodiments, the floating dosage form comprises both a sustained release dosage component and an enterically coated immediate release dosage component. In some embodiments, the floating dosage form comprises both a delayed release dosage component and an enterically coated immediate release dosage component, wherein when administered, the floating dosage form provides a pulsatile release of the API with a lag time from about 2 hours to about 14 hours.

Swellable Dosage Form

In any of the embodiments described herein, the controlled release dosage form is a dosage form that swells when exposed to gastric fluid and thereby retaining the API in the stomach of a subject treated. Various techniques for preparing a swellable dosage form are known. For example, U.S. Pat. Nos. 5,972,389 and 6,723,340 B2, incorporated by reference herein, disclose a swellable dosage form that can be utilized in the embodiments disclosed herein.

The swelling dosage form described herein can include an API and one or more swelling polymer. Suitable swelling polymers include those known in the art, for example, polyethylene oxide (e.g., Polyox 205-NF) and/or hydroxyalkyl alkylcellulose (e.g., hydroxypropyl methyl cellulose, e.g., Methocel K4M, K100M) may be used. In some embodiments, the one or more swelling polymers are a combination of poly(ethylene oxide) and hydroxypropyl methylcellulose in various weight ratios (e.g., from about 10:1 to about 1:10).

In some embodiments, the swelling dosage form is a swelling tablet (e.g., a monolithic, bilayer, or trilayer tablet) or a swelling sheet (e.g., an Accordion Pill™, in which an API, optionally coated, is embedded in one section of the swellable polymer sheets). In some embodiments, the swelling dosage form is a monolithic tablet comprising an active layer comprising an API and a swelling layer. In some embodiments, the swelling layer encapsulates the active layer. In some embodiments, the swelling dosage form is a bilayer tablet comprising an active layer comprising an API and a swelling layer. In some embodiments, more than one active layer are present in the swelling dosage form. In some embodiments, more than one swelling layer are present in the swelling dosage form.

The swellable dosage form herein may be a sustained release or delayed release dosage form.

In some embodiments, the swelling dosage form is a sustained release dosage form. In some embodiments, the API together with the swelling polymer form a swellable matrix. In some embodiments, the API is coated (e.g., seal coated, enterically coated, or a combination thereof). In some embodiments, the API in the swellable dosage form may be in an amount of about 20%, about 30%, about 40%, about 50%, about 60%, about 70%, about 80%, or any ranges thereof, by weight of total weight of the swellable dosage form. The one or more swelling polymers in the swellable dosage form may be in an amount of about 10%, about 15%, about 20%, about 25%, about 30%, about 35%, about 40%, about 45%, about 50%, or any ranges thereof, by weight of total weight of the swellable dosage form. The swellable dosage form may also include pharmaceutical excipients in an amount of about 0.1%, about 0.5%, about 1%, about 2%, about 5%, about 10%, or any ranges thereof, by weight of total weight of the swellable dosage form. For example, the swellable dosage form may be composed of about 60% coated DMF; about 24% Polyox 205-NF (PEO); about 15% Methocel K4M (HPMC); and about 1% magnesium stearate.

In some embodiments, the swellable matrix releases the API in a sustained manner over a period of from about 2 to about 24 hours (e.g., about 2 hours, about 4 hours, about 6 hours, about 8 hours, about 10 hours, about 12 hours, about 14 hours, about 16 hours, about 18 hours, about 20 hours, about 22 hours, about 24 hours, or any ranges thereof). In some embodiments, the swellable matrix exhibits zero-order release of the API.

In some embodiments, the swelling dosage form is a delayed release dosage form, which, when administered together with a second dosage form (e.g., an enterically coated immediate release dosage form, or a delayed release dosage form), provides a pulsatile release of the API with a lag time from about 2 hours to about 14 hours (e.g., about 2 hours, about 4 hours, about 6 hours, about 8 hours, about 10 hours, about 12 hours, about 14 hours, or any ranges thereof). In some embodiments, the swellable pulsatile release dosage form comprises one or more swelling polymers and an API. In some embodiments, the API is coated (e.g., seal coated, enterically coated, or a combination thereof). Suitable swellable polymers are described above.

In some embodiments, the swelling dosage form comprises both a delayed release dosage component and an enterically coated immediate release dosage component, wherein when administered, the swelling dosage form provides a pulsatile release of the API with a lag time from about 2 hours to about 14 hours.

Intestinal Retention Dosage Form

In some embodiments, the invention provides an intestinal retention dosage form for delivering an API to a subject treated. In some embodiments, the intestinal retention dosage form releases the API in the GI tract of a subject in a sustained period of time between about 0.25 and about 24 hours (e.g., about 2, about 4, about 6, about 8, about 10, about 12, about 14, about 16, about 18, about 20, about 22, or about 24 hours). Various methods for achieving intestinal retention are known, for example, via mucoadhesion or mechanical retention.

Mucoadhesive Dosage Form

In some embodiments, the intestinal retention dosage form is a mucoadhesive dosage form, which is adhesive to mucosal surface of the gastrointestinal tract (e.g., small intestine) of a subject treated. In some embodiments, the API in the mucoadhesive dosage form is retained in the small intestine of a subject treated. Various techniques for preparing a mucoadhesive dosage form are known. For example, U.S. Pat. No. 6,022,562, incorporated by reference herein, discloses microcapsules containing particles of drug that are coated with a film-forming polymer derivative, a hydrophobic plasticizer, a functional agent, and a nitrogen-containing polymer. These microparticles remain in the small intestine and release the drug over a period of time. Methods for evaluating effectiveness of mucoadhesive dosage forms are also known.

U.S. Publication No. 2004/0234601 A1, incorporated by reference herein, also discloses a mucoadhesive dosage form.

Another example of a mucoadhesive dosage form is disclosed in U.S. Pat. No. 8,298,574 B2, incorporated by reference herein.

Mucoadhesive dosage forms herein can comprise an API and one or more mucoadhesive polymers. In some embodiments, the API is seal coated, enterically coated, or seal and enterically coated. In some embodiments, the only active pharmaceutical ingredient in the mucoadhesive dosage form is DMF. Suitable mucoadhesive polymers are known and include any polymer that is or becomes adhesive to a mucosal membrane (e.g., mucosal membrane of small intestine) upon hydration. The mucoadhesive polymers can be cationic, anionic, or neutral. The mucoadhesive polymers can be natural or synthetic. The mucoadhesive polymer can be biocompatible. The mucoadhesive polymer can be water soluble or water insoluble.

Non-limiting synthetic mucoadhesive polymers suitable for the invention include, for example, poly(acrylic acid), polyvinyl alcohol, polyamides, hydroxypropyl methylcellulose (HPMC), poly(methylacrylate) derivatives, polycarbonates, polyalkylene glycols, polyvinyl ethers/esters/halides, methylcellulose (MC), sodium carboxymethylcellulose (CMC), polymethylmethacrylic acid, and hydroxypropyl cellulose (HPC).

Non-limiting biocompatible mucoadhesive polymers suitable for the invention also include, for example, cellulose based polymers, ethylene glycol polymers and its copolymers, oxyethylene polymers, polyvinyl alcohol, polyvinyl acetate, and esters of hyaluronic acid.

Non-limiting synthetic mucoadhesive polymers suitable for the invention also include, for example, cellulose derivatives (e.g., CMC, sodium CMC, thiolated CMC, hydroxylethyl cellulose (HEC), HPC, HPMC, methyl cellulose (MC), methylhydroxyethylcellulose) and poly(acrylic acid)-based polymers (e.g., polyacrylic acid (PAA), polyacrylates, poly(methylvinylether-comethacrylic acid), poly(2-hydroxyethyl methacrylate), poly(acrylic acid-co-ethylhexylacrylate), poly(methacrylate), poly(alkylcyanoacrylate), poly(isohexylcyanoacrylate), poly(isobutylcyanoacrylate), or copolymer of acrylic acid and PEG).

Non-limiting natural mucoadhesive polymers suitable for the invention include, for example, agarose, chitosan, gelatin, pectin, sodium alginate, and various gums (e.g., guar, xanthan, gellan, carrageenan).

Non-limiting cationic mucoadhesive polymers suitable for the invention include, for example, aminodextran, chitosan, trimethylated chitosan, and dimethylaminoethyl dextran.

Non-limiting anionic mucoadhesive polymers suitable for the invention include, for example, Chitosan-EDTA, Cellulose Propionate (CP), CMC, pectin, PAA, polycarbonate (PC), sodium alginate, sodium CMC, and xanthan gum.

Non-limiting neutral mucoadhesive polymers suitable for the invention include, for example, hydroxyethyl starch, HPC, poly(ethylene oxide), Poly(Vinyl Acetate) (PVA), poly(vinyl pyrrolidone) (PVP), and scleroglucan.

Non-limiting water soluble mucoadhesive polymers suitable for the invention include, for example, CP, hydroxylethylcellulose (HEC), HPC, HPMC, PAA, sodium CMC, and sodium alginate.

Non-limiting water insoluble mucoadhesive polymers suitable for the invention include, for example, chitosan, ethyl cellulose (EC), and PC.

In some embodiments, the one or more mucoadhesive polymers comprises chitosan, lectin, or a combination thereof. In some embodiments, the one or more mucoadhesive polymer can be any combination of the suitable mucoadhesive polymers described above.

In any of the embodiments described herein, the mucoadhesive dosage form may be in any suitable forms (e.g., microspheres, microparticles, nanoparticles, films, or tablets). In some embodiments, the mucoadhesive dosage form is in the form of microspheres. In some embodiments, the mucoadhesive dosage form is in the form of tablets.

In some embodiments, the mucoadhesive dosage form releases the API (e.g., DMF) in the GI tract of a subject in a sustained period of time (e.g., about 2, about 4, about 6, about 8, about 10, about 12, about 14, about 16, about 18, about 20, about 22, or about 24 hours).

Mechanical Retention

In some embodiments, the intestinal retention dosage form is a dosage form comprising a plurality of API containing microparticles having a mean diameter of about 50 microns to about 1000 microns (e.g., about 50, 100, 150, 200, 300, 400, 500, 750, 1,000 microns, or any ranges thereof) that are retained (e.g., mechanically retained) in the GI tract (e.g., small intestine) for an extended period of time from about 2 hours to about 12 hours (e.g., about 2, 3, 4, 5, 6, 7, 8, 10, 12, or any ranges thereof). In some embodiments, the API in the intestinal retention dosage form is retained in the small intestine of a subject treated. In some embodiments, the microparticles have a mean diameter of about 100 microns to about 500 microns. In some embodiments, the microparticles have a mean diameter of about 50 microns to about 500 microns. In some embodiments, the only active pharmaceutical ingredient in the intestinal retention dosage form is DMF. Methods for preparing a mechanically retained intestinal retention dosage form are known, for example, via the Micropump® method.

Unit Dosage Forms

The controlled release dosage form described herein may be provided as a unit dosage form or part of a unit dosage form or in a kit.

In some embodiments, a kit (e.g., a blister pack) comprises one or more pharmaceutical formulations, wherein the pharmaceutical formulation when orally dosed to a subject delivers to the GI tract (e.g., upper GI tract or lower GI tract) of the subject treated, the total daily dose of API, in a sustained or pulsatile manner (e.g., to the upper gastrointestinal tract or lower GI tract (e.g., small intestine) of a subject treated). In some embodiments, the kit (e.g., a blister pack) comprises at least two physically separated dosage forms (e.g., two capsules, two tablets, or one capsule and one tablet), wherein at least one of the dosage forms is a controlled release dosage form described herein. In some embodiments, the only active ingredient in the pharmaceutical formulation(s) of the kit (e.g., a blister pack) is DMF.

In some embodiments, the invention provides a unit dosage form. In some embodiments, the unit dosage form is a single unit of a controlled release dosage form described herein. In some embodiments, the unit dosage form is a combination of one or more units of a controlled release dosage form described herein and one or more units of a second dosage form (e.g., a controlled release dosage form described herein, an enterically coated immediate release dosage form, a combination thereof). In some embodiments, the controlled release dosage form is a sustained release dosage form. In some embodiments, the second dosage form is a delayed release dosage form.

In some embodiments, the unit dosage form, when orally dosed to a subject, delivers to the GI tract (e.g., upper GI tract or lower GI tract (e.g., small intestine)) of the subject treated, more than one dose of the API, in a sustained or pulsatile manner, wherein the unit dosage form comprises
(a) a first dosage component comprising a first dose of the API; and
(b) a second dosage component comprising a second dose of the API.

In some embodiments, the second dose of the API in the unit dosage form is retained in the stomach and/or small intestine of a subject treated for at least 3 hours (e.g., about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, or any ranges thereof). In some embodiments, the second dose of the API in the unit dosage form is retained in the stomach and/or small intestine for about 3 hours to about 17 hours. In some embodiments, the second dose of the API in the unit dosage form is retained in the stomach and/or small intestine of a subject treated for at least 4 hours, at least 5 hours, at least 6 hours, at least 7 hours, or at least 8 hours. In some embodiments, the second dose of the API in the unit dosage form is retained in the stomach and/or small intestine of a subject treated for at least 5 hours, at least 6 hours, or at least 7 hours.

In some embodiments, the second dosage component of the unit dosage form is a controlled release dosage form described above.

In some embodiments, the first and second dosage components may be in one dosage form (e.g., a tablet or a capsule). In some embodiments, the only active ingredients in the unit dosage form is DMF.

In some embodiments, the unit dosage form (e.g., as described herein) releases MMF, or a compound that can be metabolized into MMF in vivo, in a bimodal or multi-modal manner in which a first dose of the API after an initial delay time to provide a pulse of drug release and one or more additional doses of the API are released each after a respective lag time to provide additional pulses of drug release. In some embodiments, the pulses of drug release are delivered to the upper gastrointestinal tract of a subject treated. In some embodiments, the pulses of drug release are delivered to the lower gastrointestinal tract of a subject treated. In some embodiments, one pulse of drug release is delivered to the upper gastrointestinal tract of a subject treated and a second pulse of drug release is delivered to the lower gastrointestinal tract of the subject treated.

It may be advantageous to deliver DMF in pulses to the upper GI tract rather than to the lower GI tract for absorption. In some embodiments, the pulses of DMF are delivered to the upper gastrointestinal tract of a subject treated.

In some embodiments, the invention provides a unit dosage form that delivers MMF, or a compound that can be metabolized into MMF in vivo, in pulses to the upper GI tract upon oral administration of the unit dosage form. In some embodiments, the unit dosage form comprises
(a) a first dosage component comprising a first dose of API; and
(b) a second dosage component comprising a second dose of API;
wherein when the unit dosage form is administered to a subject orally, the first and second doses of API, are delivered to the upper GI tract of the subject in a pulsatile manner.

In some embodiments, the second dosage component of the unit dosage form is a controlled release dosage form described above.

In some embodiments, patients orally administered a unit dosage form described herein (with or without food) once daily exhibit one or more of the following pharmacokinetic parameters in the subject: (a) a mean plasma MMF $AUC_{overall}$ ranging from about 4.81 h·mg/L to about 11.2 h·mg/L; (b a mean plasma MMF $AUC_{0-12}$ ranging from about 2.4 h·mg/L to about 5.5 h·mg/L; and (c) a mean $AUC_{0\text{-}infinity}$ ranging from about 2.4 h·mg/L to about 5.6 h·mg/L. In some embodiments, the subject treated exhibits a pharmacokinetic profile characterized by both (a) and (b), both (a) and (c), or both (b) and (c). In some embodiments, the subject treated exhibits a pharmacokinetic profile characterized by (a), (b), and (c).

In some embodiments, a subject orally administered a unit dosage form described herein once daily exhibits a mean MMF plasma area under the curve 0-12 ($AUC_{0-12}$) of about 2.36 h·mg/L to about 5.50 h·mg/L, from about 2.75 h·mg/L to about 5.10 h·mg/L, or from about 3.14 h·mg/L to about 4.91 h·mg/L. In one embodiment, the subject exhibits a mean $AUC_{0-12}$ of about 3.93 h·mg/L.

In some embodiments, a subject orally administered a unit dosage form described herein (with or without food) once daily exhibits a mean MMF plasma overall area under the curve ($AUC_{overall}$) of about 4.81 h·mg/mL to about 11.2 h·mg/mL, or from about 6.40 h·mg/L to about 10.1 h·mg/L. In one embodiment, the subject exhibits a mean $AUC_{overall}$ of about 8.02 h·mg/L.

First Dosage Component

Upon oral administration of the unit dosage form to a subject, the first dosage component comprising a first dose of API, may provide the first dose, for example, as a first pulse of an API, for absorption in the upper GI tract of the subject. In any of the embodiments described herein, the first dosage component can be an enterically coated immediate release or a delayed release dosage form. In some embodiments, the only active ingredient in the first dosage component is DMF.

In some embodiments, suitable amounts of API for the first dosage component include those that can provide, by itself or in combination with one or more doses from, for example, a second dosage component, a daily amount of the respective compound ranging from about 1 mg/kg to about 50 mg/kg (e.g., from about 2.5 mg/kg to about 20 mg/kg or from about 2.5 mg/kg to about 15 mg/kg).

Suitable doses of DMF for the first dosage component may be any therapeutically effective dose, e.g., an amount that is effective in treating multiple sclerosis. For example, suitable doses of DMF for the first dosage component may be any dose from 20 mg to 1 g of DMF. In some embodiments, the suitable doses of DMF in the first dosage component may be any dose from about 80 mg to about 1000 mg of DMF. In some embodiments, the suitable doses of DMF in the first dosage component may be any dose from about 100 mg to about 750 mg of DMF. In some embodiments, the suitable doses of DMF in the first dosage component is about 200 to about 600 mg. In some embodiments, the suitable doses of DMF in the first dosage component may be any dose from about 300 to about 600 mg.

In some embodiments, the DMF in the first dosage component is about 60 mg, about 80 mg, about 100 mg, about 120 mg, about 160 mg, about 200 mg, about 240 mg, about 320 mg, about 360 mg, about 400 mg, about 480 mg, about 600 mg, about 720 mg, about 800 mg, about 900 mg, about 1000 mg of DMF, or any ranges thereof.

The first dosage component can contain an amount of a compound that that can metabolize into MMF that provides an equivalent amount of MMF as the doses of DMF described above.

Suitable first dosage component may be in a form of a micro-pellet, a microtablet, a capsule (such as a soft or hard gelatine capsule), a granulate, or a tablet. In some embodiments, the first dosage component is in the form of microtablets or micropellets (e.g., enteric-coated microtablets or micropellets). Suitable microtablets or micropellets are, without limitation, those having a mean diameter of 5,000 microns or less (e.g., 4,000 microns or less, 3,000 microns or less, 2,000 microns or less, 1,000 microns or less, or 500 microns or less) exclusive of any optional coating applied to the microtablets or micropellets. Methods for preparing microtablets or micropellets (e.g., enteric-coated microtablets or micropellets) comprising DMF are known in the art, for example, as described in U.S. Pat. No. 6,509,376 and incorporated by reference in its entirety herein.

In some embodiments, the first dosage component comprises an acid soluble outer coating. For example, in some embodiments, the first dosage component is in the form of enteric-coated microtablets or micropellets, and the enteric-coated microtablets or micropellets are encapsulated with an acid soluble coating, e.g., in a soft-shell or hard-shell gelatin capsule.

Other suitable acid soluble coatings for the first dosage component are known in the art and include those coatings that dissolve at a pH less than 6.0. Non-limiting examples of acid soluble coatings include gelatin, Eudragit® E-100, polyvinyl acetyl diethylaminoacetate, and chitosan coatings. The acid-soluble coating may be applied using various techniques (e.g., spray techniques) known to one skilled in the art.

The first dosage component may also comprise one or more pharmaceutically acceptable excipients in addition to those described above. Suitable pharmaceutically acceptable excipients are those known in the art, for example, binders, fillers, disintegrants, glidants, lubricants, diluents, plasticizers, etc. as described in Remington's Pharmaceutical Science, 18$^{th}$ Edition, 1990, Mack Publishing Company, Easton, Pa. ("Remington's").

Second Dosage Component

The second dosage component is a controlled release dosage form described above. In some embodiments, the only active ingredient in the second dosage form is DMF.

In some embodiments, suitable amounts of API for the second dosage component include those that can provide, by itself or in combination with one or more doses from, for example, a first dosage component, a daily amount of the respective compound (e.g., DMF) ranging from about 1 mg/kg to about 50 mg/kg (e.g., from about 2.5 mg/kg to about 20 mg/kg or from about 2.5 mg/kg to about 15 mg/kg).

Suitable doses of DMF for the second dosage component may be any therapeutically effective dose, e.g., an amount that is effective in treating multiple sclerosis. For example, suitable doses of DMF for the second dosage component may be any dose from 20 mg to 1 g of DMF. In some embodiments, the suitable doses of DMF in the second dosage component may be any dose from about 80 mg to about 1000 mg of DMF. In some embodiments, the suitable doses of DMF in the second dosage component may be any dose from about 100 mg to about 750 mg of DMF. In some embodiments, the suitable doses of DMF in the second dosage component is about 200 to about 600 mg. In some embodiments, the suitable doses of DMF in the second dosage component may be any dose from about 300 to about 600 mg.

In some embodiments, the DMF in the second dosage component is about 60 mg, about 80 mg, about 100 mg, about 120 mg, about 160 mg, about 200 mg, about 240 mg, about 320 mg, about 360 mg, about 400 mg, about 480 mg, about 600 mg, about 720 mg, about 800 mg, about 900 mg, about 1000 mg of DMF, or any ranges thereof.

The second dosage component can contain an amount of a compound that that can metabolize into MMF that provides an equivalent amount of MMF as the doses of DMF described above.

In some embodiments, the second dosage component comprises an acid soluble outer coating as described for the first dosage component.

Relationship of First and Second Dosage Components

In some embodiments, the first dosage component and the second dosage component are both part of a capsule. In some embodiments, the second dosage component is a floating capsule comprising an acid soluble cap (e.g., gelatin cap), and the first dosage component is placed between a pulsatile coating or layer of the second dosage component and the acid soluble cap (e.g., gelatin cap). Upon oral administration, the acid soluble cap (e.g., gelatin cap) is dissolved in the gastric fluid and releases the first dose of drug (e.g., DMF) from the first dosage component. At the same time, the second dosage component floats in the gastric fluid and is slowly eroded by the gastric fluid until a pulsatile coating or layer is disintegrated and releases the second dose of drug (e.g., DMF).

In some embodiments, the first dosage component encapsulates the second dosage component. In some embodiments, the first dosage component is further encapsulated by an acid soluble coating. In some embodiments, the second dosage component comprises an outer acid resistant coating.

In some embodiments, the first dosage component and the second dosage components are not physically attached to each other (e.g., as two capsules, two tablets, or one capsule and one tablet), which are provided (e.g., packaged) in a kit (e.g., a blister pack). For example, in some embodiments, the first dosage component is a non-gastro-retentive capsule (e.g., containing 120 mg or 240 mg DMF) and the second dosage component is a controlled release dosage form (e.g., as described herein). Thus, oral administration of the unit dosage form requires orally administering a non-gastro-retentive capsule (e.g., containing 120 mg or 240 mg DMF) and one controlled release dosage form (e.g., as described herein) at the same or substantially the same time as a single dose.

Unit Dosage Form Comprising More than Two Dosage Components

In some embodiments, the unit dosage form is configured to have more than two dosage components, e.g., to provide a sustained release, or more than two pulses of releases of the API. In some embodiments, the unit dosage form comprising the first and second dosage components further comprises one or more dosage components comprising one or more doses of the API, wherein upon oral administration of the unit dosage form to a subject, the first, second, and the one or more doses of the API, are delivered to GI tract (e.g., upper GI tract or lower GI tract) of the subject in a sustained or pulsatile manner. The time between two consecutive pulses (e.g., between the first and second pulse, or the second and third pulses, etc.) in a pulsatile delivery system may be the same or different, each may be about 2 hours, about 4 hours, about 6 hours, about 8 hours, about 10 hours, about 12 hours, about 14 hours, or any ranges thereof.

Method of Treatment

DMF and its active metabolite MMF have been indicated as useful for the treatment or prophylactic treatment of various diseases or disorders. Thus, in some embodiments, the invention also provides a method of treatment or prophylactic treatment of diseases or disorders where administering DMF is helpful, the method comprising orally administering to a subject in need thereof a unit dosage form (e.g., as described herein) once per day (i.e., QD dosing). The treatment or prophylactic treatment may be acute or chronic (e.g., more than 1, 2, 3, 4, 5, 8, 10, or 12 weeks) treatments.

In some embodiments, the disease or disorder where administering DMF is helpful is (1) an autoimmune disease selected from the group consisting of polyarthritis, rheumatoid arthritis, multiple sclerosis, graft-versus-host reactions, juvenile-onset diabetes, Hashimoto's thyroiditis, Grave's disease, systemic Lupus erythematodes (SLE), Sjogren's syndrome, pernicious anaemia and chronic active (=lupoid) hepatitis, psoriasis, psoriatic arthritis, neurodermatitis and enteritis regionalis Crohn;

(2) a mitochondrial disease selected from the group consisting of Parkinson syndrome, Alzheimer's disease, Chorea Huntington disease, retinopathia pigmentosa or forms of mitochondrial encephalomyopathy;

(3) a NF-kappaB mediated diseases selected from the group consisting of progressive systemic sclerodermia, osteochondritis syphilitica (Wegener's disease), cutis marmorata (livedo reticularis), Behcet disease, panarteriitis, colitis ulcerosa, vasculitis, osteoarthritis, gout, artenosclerosis, Reiter's disease, pulmonary granulomatosis, types of encephalitis, endotoxic shock (septic-toxic shock), sepsis, pneumonia, encephalomyelitis, anorexia nervosa, hepatitis (acute hepatitis, chronic hepatitis, toxic hepatitis, alcohol-induced hepatitis, viral hepatitis, jaundice, liver insufficiency and cytomegaloviral hepatitis), Rennert T-lymphomatosis, mesangial nephritis, post-angioplastic restenosis, reperfusion syndrome, cytomegaloviral retinopathy, adenoviral diseases such as adenoviral colds, adenoviral pharyngoconjunctival fever and adenoviral ophthalmia, AIDS, Guillain-Barré syndrome, post-herpetic or post-zoster neuralgia, inflammatory demyelinising polyneuropathy, mononeuropathia multiplex, mucoviscidosis, Bechterew's disease, Barett oesophagus, EBV (Epstein-Barr virus) infection, cardiac remodeling, interstitial cystitis, diabetes mellitus type II, human tumour radiosensitisation, multi-resistance of malignant cells to chemotherapeutic agents (multidrug resistance in chemotherapy), granuloma annulare and cancers such as mamma carcinoma, colon carcinoma, melanoma, primary liver cell carcinoma, adenocarcinoma, kaposi's sarcoma, prostate carcinoma, leukaemia such as acute myeloid leukaemia, multiple myeloma (plasmocytoma), Burkitt lymphoma and Castleman tumour;

(4) a cardiovascular disease selected from the group consisting of cardiac insufficiency, myocardial infarct, angina pectoris and combinations thereof;

(5) a respiratory disease selected from the group consisting of asthma, chronic obstructive pulmonary diseases, PDGF-induced thymidine uptake of bronchial smooth muscle cells, bronchial smooth muscle cell proliferation, and combinations thereof;

(6) a neurodegeneration or neuroinflammation selected from the group consisting of Adrenal Leukodystrophy (ALD), Alcoholism, Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cerebral palsy, Cockayne syndrome, Corticobasal degeneration, Creutzfeldt-Jakob disease, Familial Fatal Insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseases, Progressive Supranuclear Palsy, Refsum's disease, Sandhoff disease, Schilder's disease, Subacute combined degeneration of spinal cord secondary to Pernicious Anaemia, Spielmeyer-Vogt-Sjögren-Batten disease (also known as Batten disease), Spinocerebellar ataxia, Spinal muscular atrophy, Steele-Richardson-Olszewski disease, Tabes dorsalis, Toxic encephalopathy, LHON (Leber's Hereditary optic neuropathy), MELAS (Mitochondrial Encephalomyopathy; Lactic Acidosis; Stroke), MERRF (Myoclonic Epilepsy; Ragged Red Fibers), PEO (Progressive External Opthalmoplegia), Leigh's Syndrome, MNGIE (Myopathy and external ophthalmoplegia; Neuropathy; Gastro-Intestinal; Encephalopathy), Kearns-Sayre Syndrome (KSS), NARP, Hereditary Spastic Paraparesis, Mitochondrial myopathy, and Friedreich Ataxia; or (7) a demyelinating neurological disorder selected from the group consisting of optic neuritis, acute inflammatory demyelinating polyneuropathy (AIDP), chronic inflammatory demyelinating polyneuropathy (CIDP), acute transverse myelitis, progressive multifocal leucoencephalopathy (PML), acute disseminated encephalomyelitis (ADEM) or other hereditary disorders (e.g., leukodystrophies, Leber's optic atrophy, and Charcot-Marie-Tooth disease).

In some embodiments, the disease or disorder where administering DMF is helpful is a neutrophil mediated disease or disorder (e.g., an allergic disease or disorder, an inflammatory disease or disorder, an autoimmune disease or disorder, or a tumor).

Non-limiting examples of autoimmune diseases or disorders include autoimmune Addison's disease, autoimmune hemolytic anemia, autoimmune hepatitis, autoimmune inner ear disease, autoimmune lymphoproliferative syndrome (ALPS), autoimmune thrombocytopenic purpura (ATP), or autoimmune skin blistering diseases (AIBD).

Non-limiting examples of autoimmune skin blistering diseases include epidermolysis bullosa acquistita (EBA), pemphigoid disease (e.g., bullous pemphigoid, mucous membrane pemphigoid, or pemphigoid gestationis), IgA-mediated bullous dermatoses (e.g., Dermatitis Herpetiformis or Linear IgA Bullous Dermatosis), and pemphigus disease (e.g., IgA Pemphigus).

Non-limiting neutrophil mediated diseases or disorders also include an inflammatory skin or subcuteneous disease selected from the group consisting of Pyoderma Gangrenosum, Erosive Pustular Dermatosis of the Scalp, Sweet's Syndrome, Bowel-associated Dermatosis-arthritis Syndrome, Pustular Psoriasis, Acute Generalized Exanthematous Pustulosis, Keratoderma Blenorrhagicum, Sneddon-Wilkinson Disease, Amicrobial Pustulosis of the Folds, Infantile Acropustulosis, Transient Neonatal Pustulosis, Neutrophilic Eccrine Hidradenitis, Rheumatoid Neutrophilic Dermatitis, Neutrophilic Urticaria, Still's Disease, Erythema Marginatum, Unclassified Periodic Fever Syndromes/Autoinflammatory Syndromes, Bullous Systemic Lupus Erythematosus, and Neutrophilic Dermatosis of the Dorsal Hands (Pustular Vasculitis);

Non-limiting neutrophil mediated diseases or disorders also include:
a) an allergic condition selected from the group consisting of anaphylaxis, allergic rhinitis and allergic asthma;
b) neutrophil mediated respiratory disease selected from the group consisting of lung cancer, severe asphyxic episodes of asthma, acute lung injury, and Acute Respiratory Distress Syndrome;
c) an acute tissue injury selected from the group consisting of acute kidney injury, ischemia reperfusion injury, sepsis, and septicemia with multiorgan failure;
d) an inflammatory bowel disease selected from the group consisting of ulcerative colitis, Crohn's disease, and indeterminate colitis; and
e) sickle cell crisis or acute chest syndrome.

In some embodiments, the disease or disorder where administering DMF is helpful is a disease or disorder that is associated with aberrant PI3K/AKT signaling including cancer, chronic inflammation and allergy, neurodegerative disease, cardiovascular disease and metabolic diseases. Non-limiting examples of disease or disorders that are associated with aberrant PI3K/AKT signaling include all forms of cancer, precancerous lesions, cardiovascular disease, rheumatologic disease, pulmonary disease, dermatologic disease, gynecological diseases, vascular disease, neurologic disease, and infectious disease including bacterial, viral, retroviral, and parasitic diseases. In some embodiments, the disease or disorder to be treated is cancer. Non-limiting examples of cancer include breast cancer, lung cancer, ovarian cancer, uterine cancer, brain cancer, sarcoma, melanoma, leukemia, lymphoma, colorectal cancer, prostate cancer, and liver cancer. In some embodiments, the disease or disorder to be treated is rheumatologic disease, e.g., rheumatoid arthritis or osteoarthritis. In some embodiments, the disease or disorder to be treated is pulmonary disease, e.g., allergic rhinitis, chronic obstructive pulmonary disease (COPD).

In some embodiments, the disease or disorder where administering DMF is helpful is a disease or disorder that is associated with aberrant p38 MAPK signaling. Non-limiting examples of such diseases include COPD (including chronic bronchitis and emphysema), asthma, paediatric asthma, cystic fibrosis, sarcoidosis, idiopathic pulmonary fibrosis, allergic rhinitis, rhinitis, sinusitis, allergic conjunctivitis, conjunctivitis, allergic dermatitis, contact dermatitis, psoriasis, ulcerative colitis, inflamed joints secondary to rheumatoid arthritis or osteoarthritis, rheumatoid arthritis, pancreatitis, cachexia, inhibition of the growth and metastasis of tumours including non-small cell lung carcinoma, breast carcinoma, gastric carcinoma, colorectal carcinomas and malignant melanoma.

In some embodiments, the invention provides a method of treating multiple sclerosis (e.g., relapsing-remitting MS, secondary progressive MS, primary progressive MS, progressive relapsing MS) in a subject in need thereof, wherein the method comprises administering to the subject a controlled release dosage form or an unit dosage form (e.g., as described herein) once per day.

In some embodiments, the unit dosage form comprises (a) a first dosage component comprising a first dose of about 80 mg to about 360 mg (e.g., about 120 mg or about 240 mg) of an API; and (b) a second dosage component comprising a second dose of about 80 mg to about 720 mg (e.g., about 120 mg or about 240 mg) of the API;

wherein when the unit dosage form is administered to a subject orally, the first and second doses of the API are delivered to the upper GI tract of the subject in a sustained or pulsatile manner.

In any of the embodiments described herein, the controlled release dosage form or unit dosage form may be administered to a subject with or without food.

In some embodiments, the first and second dosage components of the unit dosage form are physically separated from each other (e.g., as two capsules, two tablets, or one capsule and one tablet) and are provided in a kit (e.g., a blister pack). In some embodiments, the first and second dosage components of the unit dosage form are both part of one dosage form (e.g., a pill, a tablet, or a capsule).

In some embodiments, the only active ingredient in the controlled release dosage form or unit dosage form is DMF.

In some embodiments, the method comprises orally administering to the subject the controlled release dosage form or unit dosage form with or without food once per day, wherein the subject exhibits one or more of the following pharmacokinetic parameters: (a) a mean plasma MMF $AUC_{overall}$ ranging from about 4.81 h·mg/L to about 11.2 h·mg/L; (b) a mean plasma MMF $AUC_{0-12}$ ranging from about 2.4 h·mg/L to about 5.5 h·mg/L; and (c) a mean $AUC_{0-infinity}$ ranging from about 2.4 h·mg/L to about 5.6 h·mg/L. In some embodiments, the subject treated exhibits a pharmacokinetic profile characterized by both (a) and (b), both (a) and (c), or both (b) and (c). In some embodiments, the subject treated exhibits a pharmacokinetic profile characterized by (a), (b), and (c).

In some embodiments, the subject exhibits a mean MMF plasma area under the curve 0-12 ($AUC_{0-12}$) of about 2.36 h·mg/L to about 5.50 h·mg/L, from about 2.75 h·mg/L to about 5.10 h·mg/L, or from about 3.14 h·mg/L to about 4.91 h·mg/L. In some embodiments, the subject exhibits a mean $AUC_{0-12}$ of about 3.93 h·mg/L.

In some embodiments, the subject exhibits a mean MMF plasma overall area under the curve ($AUC_{overall}$) of about 4.81 h·mg/mL to about 11.2 h·mg/mL, or from about 6.40 h·mg/L to about 10.1 h·mg/L. In some embodiments, the subject exhibits a mean $AUC_{overall}$ of about 8.02 h·mg/L.

EXAMPLES

Example 1

Preparation of Coated Pulsatile Microtablets

Figure 1A:
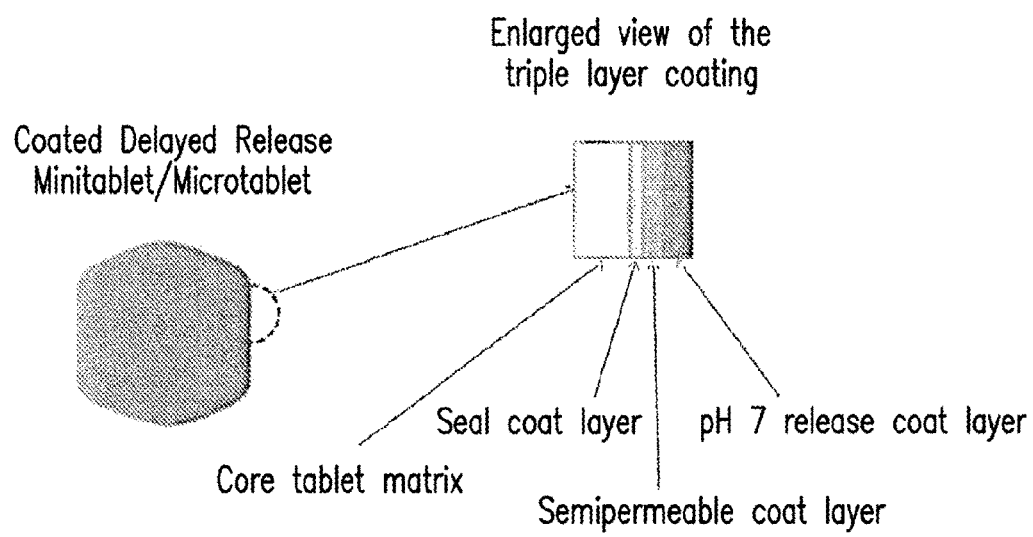

Multiple coating layers were applied onto core microtablets in order to provide a fast and complete release after a predefined delay time anywhere from 4 to 12 hours. See FIG. 1A. The core microtablets, ~2 mm in diameter and ~2 mm in thickness, were coated with a seal coating layer from 2% to 20% weight gain with respect to core microtablet weight. The seal coating (inner coating), which is based on either an enteric polymer such as Eudragit series polymers or a polyethylene glycol, was applied in order to minimize potential loss of active through sublimation during subsequent coatings. The seal coated microtablets were then coated with a semipermeable, rupture-able membrane for pulsatile release characteristics. The pulse release coating consisted of a water-insoluble polymer, either ethylcellulose (EC) or cellulose acetate (CA), and a water-soluble polymer, either hydroxypropyl cellulose (HPC, Klucel JF) or polyethylene glycol (PEG). The weight gain for pulsatile coating was around 5% to 20%. A third coating, with a target weight gain of 5% to 20%, was applied onto the pulsatile coated microtablets. The third coating, based on enteric polymer such as Eudragit FS 30D from Evonik, was intended to have pH 7.0 enteric release characteristics for colonic delivery.

Coating Solution/Suspension Preparations:
a) Inner coating solution—6.6% Eudragit L100/Triethyl citrate (w/w, 100/10) in isopropyl alcohol. Add 210 g Eudragit L100 into 1494 g IPA, stir until a clear or slightly hazy solution is formed; Add 46 g water, and mix well; Add 21 g triethyl citrate, and mix well; Add 1729 g IPA to the solution above, and stir to mix well.
b) Pulsatile coating solution—6% Ethylcellulose (EC)/Hydroxypropylcellulose (HPC) (w/w, 60/30, 65/35, 70/30) in isopropyl alcohol/water. Example given here is for EC/HPC of 65/35 only. Dissolve 74 g hydroxypropylcellulose in 395 g water; Dissolve 137 g ethylcellulose in 2895 g IPA; Mix both solutions for the final coating solution.
c) Enteric coating suspension—20% Eudragit FS 30D in aqueous suspension. Homogenize 129 g talc and 13 g triethyl citrate in 998 g water for 20 minutes; Add talc suspension slowly into 860 g Eudragit FS 30D dispersion while stirring gently; Pass the suspension preparation through a 0.5 mm sieve for the final coating suspension.

Manufacturing Steps:
a) Core microtablets. Core microtablets were prepared by conventional tablet press equipped with multi-tip microtablet toolings. Powder blends were prepared by direct blends of API with excipients.
b) Inner coating. Inner coating of Eudragit L100/triethyl citrate was applied to the core microtablets via a fluid bed coater with a Wurster column. A non-perforated pan coater was also found suitable for the coating. Microtablet weight gains were monitored throughout the coating process.
c) Pulsatile coating. Pulsatile coating of Ethylcellulose/Hydroxypropylcellulose was applied to the core microtablets via a fluid bed coater with a Wurster column. A non-perforated pan coater was also found suitable for the coating. Microtablet weight gains were monitored throughout the coating process.
d) Enteric coating. Enteric coating of Eudragit FS30D was applied to the core microtablets via a fluid bed coater with a Wurster column. A non-perforated pan coater was also found suitable for the coating. Microtablet weight gains were monitored throughout the coating process.

Test Protocol for In-Vitro Dissolution on Microtablets:
a) For group of microtablets. USP apparatus II (paddle), 100 rpm, 37° C., 2 hours in pH 0.1N HCl, followed by 10 hours in pH 7.4 phosphate buffer (USP)
b) For single microtablet. USP apparatus IV (flow through cell), 37° C., 8 mL/min, pH 7.4 phosphate buffer (USP).

Results:
Coating was successfully applied on a fluid bed coater with Wurster column insert and a non-perforated pan coater.

Microtablets coated with all three coating layers: inner coating, pulsatile coating, and top enteric coating.

Core microtablets with different disintegrant levels, 5% and 7%, were coated in order to evaluate potential effects on lag time prior to coating rupture as well as the speed of release after coating rupture.

Inner coatings were varied from 2% to 15% weight gain with Eudragit L100 with or without the presence of triethyl citrate (TEC).

Pulsatile coatings were tested using mixed polymer of ethylcellulose/hydroxypropyl cellulose with EC:HPC (w:w) polymer ratios of 60:40, 65:35, and 70:30. Coating weight gains of 3% to 20% were studied.

Enteric coatings were performed using Eudragit FS 30D enteric polymer dispersion. A weight gain of 5% to 20% was studied.

Characterization on the coated microtablets was performed using scanning electric microscope (SEM), disintegration and various in-vitro dissolution techniques.

Pulsatile release was obtained with the 3-layer coating system. Lag (delayed release) times of 0.5-6 hours were achieved with the combination of pulsatile coating and inner coating alone. Additional top coating with pH 7.0 enteric polymer resulted in additional 4-6 hours delay time. As a result, the coating system delivered 4 to 12 hours delayed release time.

Figure 1B:
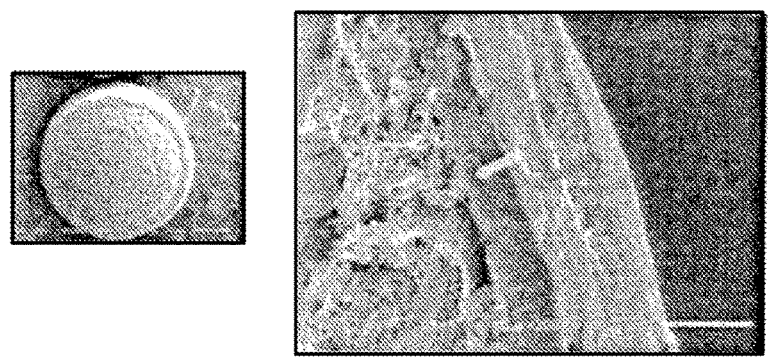

FIG. 1B shows a picture and a microscopic view of a delayed release tablet prepared according to this example with three coating layers: an inner seal coating layer, a semipermeable coating layer, and an outer pH 7 release coating layer.

Figure 2A:
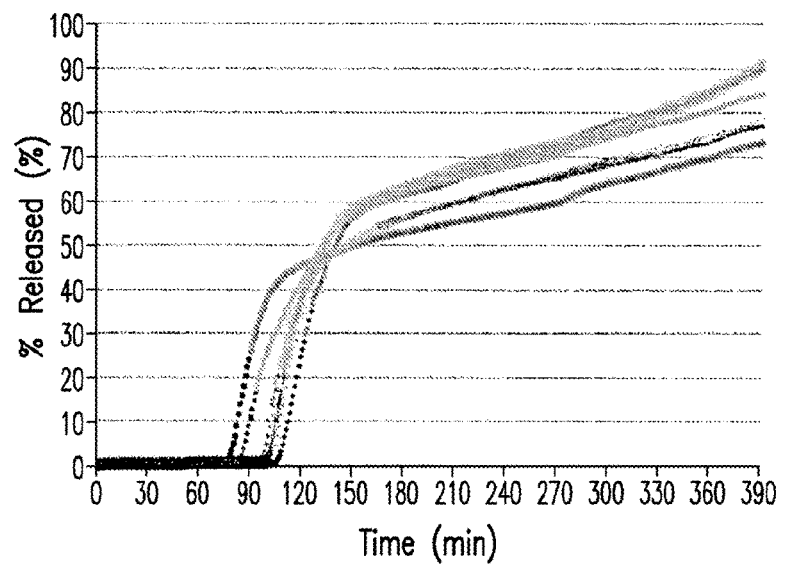
FIG. 2A shows the in vitro dissolution profile of six microtablets of one formulation tested according to United States Pharmacopeia apparatus II (paddle), 100 rpm, 37° C., 2 hours in pH 0.1N HCl, followed by 10 hours in pH 7.4 phosphate buffer (USP).

FIG. 2A shows the in vitro dissolution profile of six microtablets of one formulation.

Figure 2B:
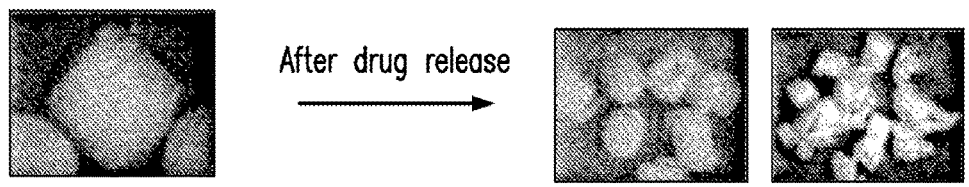
FIG. 2B shows screen shots of delayed release tablets prepared according to Example 1 before and after drug release.
Figure 3:
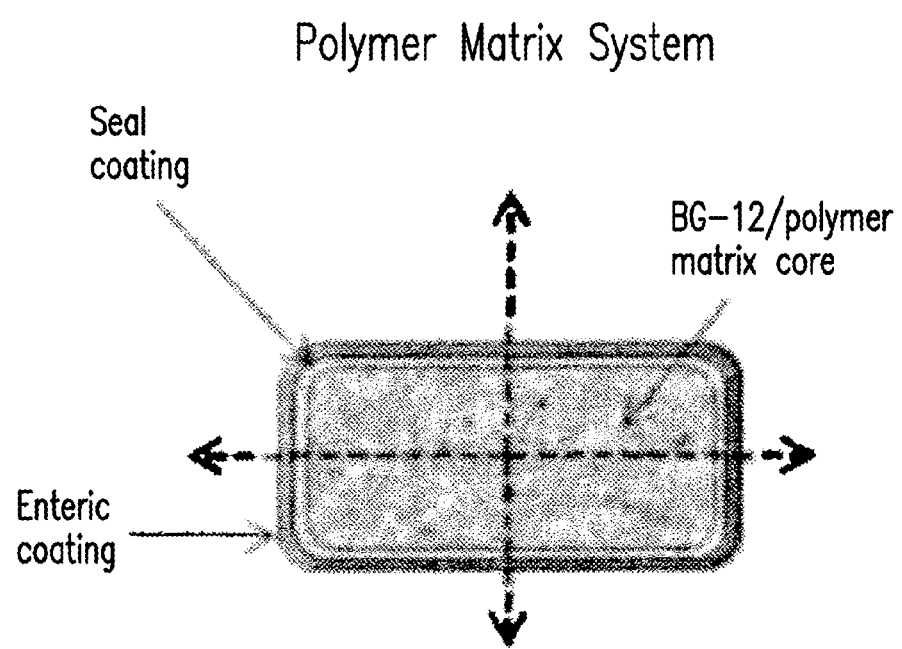
FIG. 3 shows a design of a polymer matrix system which contains a core containing DMF and a polymer, a seal coating encapsulating the core, and an outer enteric coating. In this design, DMF may be released through matrix erosion over a sustained period of time (e.g., about 6 hours).

FIG. 2B shows screen shots of a pulsatile formulation before and after drug release.

Example 2

API Particle Coating

DMF particle coating can be either coated with enteric or other release modifying coating. Coated DMF particles could be filled into capsules directly for final dosage forms. Enteric coated APIs could be formulated into tablets or capsules, and therefore no additional enteric coating will be necessary for enteric protection of the final dosage forms. These formulations have fewer tendencies for any potential dose dumping. Fluid bed coater with Wurster column insert and bottom spray or top spray can be used for DMF particle coating.

Coating Solution:
Coating Solution in IPA (L100/TEC 6.6% w/w)

| Ingredients | Batch quantity (g) |
| --- | --- |
| Eudragit L100 | 210 |
| IPA | 1494 |
| Water | 46 |
| Triethyl citrate | 21 |
| IPA | 1729 |
| TOTAL | 3500 |

A coating solution containing Eudragit L100 and triethyl citrate (TEC) in 6.6% w/w ratio was prepared by the following process. First, 210 g Eudragit L100 was added into 1494 g IPA while stirring. The resulted mixture is either a clear solution or slightly hazy. This mixture was then mixed with 46 g of water and 21 g TEC consecutively. Finally, 1729 g IPA was added to the solution and mixed to afford the coating solution.

Coating:
DMF particle coating was performed with a fluid bed coater using bottom spray (Wurster). 658 g DMF particles (mesh cut #40/#60 with 0.25% SiO2 added) was coated with 1408 g of the coating solution prepared above with the following process parameter. Atomization pressure was set at 2 bar, inlet temperature as needed, product temperature was set at about 33° C., out let temperature was set at about 30° C., pump rate was set at 2.5 g/minute.

Fluid Bed Coating—Under Coat
(Eudragit L100/TEC)

as described above. The coating weight gains were from 9% to 20%. DMF particle sizes of 130 μm to ~350 μm were also successfully coated with either Ethyl cellulose (EC)/Hydroxylpropyl cellulose (HPC) or Cellulose acetate/Polyethylene glycol (PEG) coatings. The coating weight gains were from 9% to 20%.

Batch number: 17252-131
Description: Coated Crystals (seal coating)

| Coating substrate | Substrate: Drug Substance Crystals (#40/#60 mesh cut) Substrate batch #: lot I12JS4281) Substrate quantity: 658 grams |
|---|---|

PROCESS PARAMETERS

| | Start | SPRAYING | | | | | | | | | | | Drying |
|---|---|---|---|---|---|---|---|---|---|---|---|---|---|
| Time (HH:MM) | 9:32 | 10:02 | 10:32 | 11:02 | 11:32 | 12:02 | 13:32 | 14:02 | 14:32 | 15:03 | 15:32 | 16:02 | 16:07 |
| Time (min.) | 0 | 30 | 60 | 90 | 120 | 150 | 240 | 270 | 300 | 330 | 360 | 390 | 5 |
| Air Flow Set (m3/min) | 13 | 13 | 13 | 13 | 13 | 13 | 13 | 13 | 13 | 13 | 13 | 13 | 13 |
| Inlet Air temperature Set (° C.) | 45 | 45 | 45 | 45 | 45 | 45 | 45 -> 40 | 40 -> 38 | 38 | 38 | 38 | 38 | 38 |
| Inlet Air temperature (° C.) | 55 | 44 | 59 | 53 | 44 | 64 | 53 | 58 | 38 | 43 | 53 | 53 | — |
| Core Temperature (° C.) | 34 | 34 | 37 | 36 | 34 | 36 | 36 | 34 | 33 | 33 | 34 | 32 | — |
| Outlet Air Temperature (° C.) | 29 | 29 | 30 | 30 | 30 | 31 | 32 | 30 | 30 | 30 | 30 | 30 | — |
| Spray rate Set | 4 | 4 | 4 | 5 -> 6 | 6 | 6 | 6 | 6 | 6 | 6 | 6 | — | — |
| Spay rate (ml/min) | 0 | 1.9 | 1.9 | 2.7 | 5.4 | 3.4 | 3.4 | 4.8 | 3.4 | 3.4 | 3.6 | — | — |
| Spay pressure (bar) | 2 | 2 | 2 | 2 | 2 | 2 | 2 | 2 | 2 | 2 | 2 | 2 | — |
| Amount solution consumed (g) | — | 56.5 | 114.2 | 195.9 | 356.6 | 458 | 768 | 911.3 | 1014.1 | 1117.4 | 1225.7 | 1408 | 1408 |

The coated DMF particles was dried for 5 minutes and samples were taken for testing. Coated DMF samples were characterized by both Scanning electron microscope (SEM) and in-vitro dissolution techniques.

Results

The weight of the coated DMF particle was determined to be 42.53 mg. The amount of DMF in these coated particles were calculated to be 35.09 mg. Thus, the coating weight gain here was determined to be 21.2%.

In vitro dissolution of the coated API particles were determined by USP paddle method in 0.1 N HCl solution at 100 rpm, n=3. The table below shows the dissolution rate of the coated API.

| | Vessel # | | | 17252-131 | |
|---|---|---|---|---|---|
| Time Point Label min | 1 17252-131 (14%)_1 | 2 17252-131 (14%)_2 | 3 17252-131 (14%)_3 | (14%)_AVE AVE 1, 2, 3 | SD 1, 2, 3 |
| 0 | 0.00 | 0.00 | 0.00 | 0.0% | 0.0% |
| 10 | 0.06 | 0.08 | 0.12 | 8.4% | 3.2% |
| 120 | 0.20 | 0.22 | 0.31 | 24.2% | 6.1% |
| 135 | 0.22 | 0.24 | 0.33 | 26.3% | 6.2% |
| infinite 250 rpm @ 2 hr 15 min | | | | | |

AVE: Average; SD: Standard Deviation.

Conclusion:

Coating DMF particles can be successful done on a fluid bed coater.

DMF particle sizes of ~130 μm to ~350 μm were successfully coated with Eudragit L100/TEC using similar methods Addition of 0.25% (w/w) colloidal SiO$_2$ to DMF particles prior to fluid bed coating greatly improved the powder bed flowability, and thus ensured a uniform coating of the particles.

Example 3

Osmotic Dosage Form

An example of an osmotic dosage form composition is as below that can be manufactured using dry blending, dry granulation, or wet granulation process:

Monolithic Tablet (Weight 502.6 mg):

| DMF | Drug Substance | 47.75% |
|---|---|---|
| Sorbitol | Osmotic Agent | 40.00% |
| HEC 250H or 250L | Rate Controlling Polymer | 8.00% |
| HPC EF | Binder | 3.00% |
| Silicon Dioxide | Glidant | 0.125% |
| SLS | Wetting Aid | 0.125% |
| Mg-Stearate | Lubricant | 1.00% |

Coating (Semi-Permeable Membrane Weight Gain~10% of Tablet)

| Cellulose Acetate 320 | 3.0% |
|---|---|
| Hydroxypropyl Cellulose EF | 1.0% |
| Acetone | 86.4% |
| Water | 9.6% |

Example 4

Capsule Containing One Immediate Release Tablet and Two Osmotic Tablets

Immediate Release Tablet

TABLE 1

| | IR tablet WT (mg) 275 | | | |
|---|---|---|---|---|
| | INTRA % | PERCENT | MG/ TAB | BATCH(g) 25.0 GRAMS |
| MATERIAL | | | | |
| DMF | 99.00 | 87.270 | 240.0 | 21.8 |
| COLLOIDAL SILICON DIOXIDE | 0.75 | 0.661 | 1.8 | 0.2 |
| SLS | 0.25 | 0.220 | 0.6 | 0.1 |
| PREBLEND | 100.00 | | | |
| MCC AVICEL PH105 | | 5.848 | 16.1 | 1.5 |
| AC-DI-SOL | | 5.000 | 13.8 | 1.3 |
| MAG-STEARATE | | 1.000 | 2.8 | 0.3 |
| | | 100.000 | 275.0 | 25.0 |
| SEAL COATING % SOLIDS | 5 | | | |
| MEMBRANE MATERIAL | | | | |
| EUDRAGIT L100 | 75.00 | 3.750 | | 0.9 |
| TEC | 25.00 | 1.250 | | 0.3 |
| Solids | 100.00 | | | |
| IPA | 100.00 | 95.000 | | 23.8 |
| Water | 0.00 | 0.000 | | 0.0 |
| Solvent | 100.00 | 100.000 | | 25.0 |
| ENTERIC COATING % SOLIDS | 30 | | | |
| ENTERIC MATERIAL | | | | |
| EUDRAGIT FS 30D | 96.77 | 29.031 | | 7.3 |
| T20 | 3.23 | 0.969 | | 0.2 |
| Solids | 100.00 | | | |
| IPA | 0.00 | 0.000 | | 0.0 |
| Water | 100.00 | 70.000 | | 17.5 |
| Solvent | 100.00 | 100.000 | | 25.0 |

Osmotic Tablet

TABLE 2

| | Osmotic Tablet WT (mg) 275 | | | |
|---|---|---|---|---|
| | INTRA % | PERCENT | MG/ TAB | BATCH(g) 25.0 GRAMS |
| MATERIAL | | | | |
| DMF | 99.00 | 43.640 | 120.0 | 10.9 |
| COLLOIDAL SILICON DIOXIDE | 0.75 | 0.331 | 0.9 | 0.1 |
| SLS | 0.25 | 0.110 | 0.3 | 0.0 |
| PREBLEND | 100.00 | | | |
| SORBITOL | | 43.919 | 120.8 | 11.0 |
| HEC 250H OR 250 L | | 8.000 | 22.0 | 2.0 |
| HPC EXF | | 3.000 | 8.3 | 0.8 |
| MAG-STEARATE | | 1.000 | 2.8 | 0.3 |
| | | 100.000 | 275.0 | 25.0 |
| MEMBRANE COATING % SOLIDS | 5 | | | |
| MEMBRANE MATERIAL | | | | |
| CA-320 | 75.00 | 3.750 | | 0.9 |
| HPC EF | 25.00 | 1.250 | | 0.3 |
| Solids | 100.00 | | | |
| Acetone | 90.00 | 85.500 | | 21.4 |
| Water | 10.00 | 9.500 | | 2.4 |
| Solvent | 100.00 | 100.000 | | 25.0 |

Example 5

Matrix Microtablet Dosage Form

| Component | Formulation 090913A | Formulation 090913B | Formulation 090913C | Formulation 090913D | Formulation 090913E |
|---|---|---|---|---|---|
| DMF | 59.4% | 59.4% | 59.4% | 59.4% | 59.4% |
| Flowlac 100 | 29.7% | 19.8% | 19.8% | 29.7% | 19.8% |
| HPMC K 4M | 0.0% | 19.8% | 0.0% | 0.0% | 0.0% |
| HPMC K 100M | 0.0% | 0.0% | 19.8% | 0.0% | 0.0% |
| Kollidon SR | 0.0% | 0.0% | 0.0% | 9.9% | 19.8% |
| Ethocel 10 | 9.9% | 0.0% | 0.0% | 0.0% | 0.5% |
| Magnesium Stearate | 0.5% | 0.5% | 0.5% | 0.5% | 0.5% |
| Aerosil | 0.5% | 0.5% | 0.5% | 0.5% | 0.5% |

Formulation 090913F: DMF, 46%; Lactos Fast Flo, 22%; HPMC K100LV, 30%; Aerosil 200, 0.5%; and Magnesium Stearate, 1%.

Formulation 090913G: DMF, 46%; DCP anhydrous, 22.5%; HPMC K4M, 30%; Aerosil 200, 0.5%; and Magnesium Stearate, 1%.

A brief procedure for preparing formulations 090913A-G is below.

Pass the DMF through a Co-mil U5 using a round impeller and a 7L039R conical plate. Run the mill at approximately 2400 rpm. Return the milled material to the blender. Charge the pre-weighed matrix filler and aerosil and blend the mixture for 15 min at 25 RPM minutes. Charge the blender with the pre-weighed magnesium stearate and blend for 2 minutes. Tablet half the final blend on a Picola press using 16 micro-tipped tools 8 mg weight. Adjust the compression force to required compression force. Record IPC measurements on run sheet. Tablet the second half into monolithic tablets 550 mg tablet weight—9 mm.

Example 6

Matrix Microtablet or Tablet Formulation

Formulation 101413F Drug load (DL)=65%

| Ingredient | Amount (grams) |
|---|---|
| DMF - | 1300 |
| Flowlac - | 580 |

-continued

| Ingredient | Amount (grams) |
|---|---|
| Kollidon SR - | 100 |
| Magnesium Stearate - | 10 |
| Aerosil - | 10 |
| Total - | 2000.0 |

Formulation 101413G DL=50%

| Ingredient | Amount (grams) |
|---|---|
| DMF - | 1000 |
| DCP anhydrous - | 400 |
| HPMC K4M - | 580 |
| Magnesium Stearate | 10 |
| Aerosil | 10 |
| Total | 2000.0 |

Procedure: Pass the DMF through a Comil U5 using a round impeller and a 7L039R conical plate. Run the mill at approximately 2400 rpm. (You can comil all the API and dispense the required amount per each lot). Charge the DMF, pre-weighed matrix fillers and aerosil and blend the mixture for 15 min at 25 RPM. Charge the blender with the pre-weighed magnesium stearate and blend for 2 minutes. Tablet half the final blend on a Piccola press using 16 micro-tipped tools 8 mg weight. Adjust the compression force to required compression force 5 kN @15 rpm. Record IPC measurements on run sheet. Save the second half of the blend. For tableting on the 10 mm round flat faced tablets.

Manufactured the blend formulations above and compressed them into microtablets and 10 mm round flat face tablets.

In vitro dissolution were performed according to USP apparatus II (paddle) at an agitation speed of 75 rpm. The parameters are shown below:

| Dissolution Parameters | | | |
|---|---|---|---|
| Method No.: | | Apparatus: | 2 |
| Medium: | Water | Agitation (rpm): | 75 |
| Volume (mL): | 500 | Temp. (° C.): | 37 |
| Dilution Factor (mL) | 40 | | |

FIG. 4 shows in vitro dissolution profile of six different matrix formulations. Formulations 090913A, 090913F, 101413F and 101413G each contains a plurality of microtablets. Formulations 101413FT and 101413GT have the same ingredients as 101413F and 101413G, respectively, but are made as monolithic tablets.

Example 7

Bilayer Floating Tablet

Floating tablets for sustained release: 10 mm pellets with 50-200 mg of floating layer and 400 mg of active layer are made using 10-mm punch and die and a manual pellet press. The force applied is about 1500 lb and 2000 lb.

For example, the active layer and floating layer have the following ingredients:
Active Layer:
60% coated DMF
24% Plyox 205-NF (PEO)
15% Methocel K4M (HPMC)
1% magnesium stearate
Floating Layer:
25% sodium bicarbonate
75% Methocel K100M (HPMC)

Floating tablets for pulsatile release: 10 mm pellets with 50-200 mg of floating layer and 200-300 mg of active layer are made using 10-mm punch and die and a manual pellet press. The force applied is about 1500 lb and 2000 lb.

For example, the active layer and floating layer can have the following ingredients:
Active layer: 90% coated API of DMF
10% Methocel E3 LV (HPMC)
Floating layer: 25% Sodium Bicarbonate
75% Methocel K100M (HPMC).

Example 8

Swellable Tablets

Swellable Tablets for Sustained Release:
A mixture of 60% coated DMF, 24% Polyox 205-NF (PEO), 15% Methocel K4M (HPMC), and 1% magnesium stearate will be prepared according to the procedure below.

10 mm pellets weighed about 400 mg (active+swelling layer) are made using 10-mm punch and die and a manual pellet press. The force applied is about 1500 lb and 2000 lb.

Swellable Tablets for Pulse Release Mechanism
The same procedure above is sued for preparing a swellable tablets for pulse release mechanism except that the tablet includes 312 mg of the active layer and 200 mg of the swelling layer.
Active layer: 90% coated API of DMF; 10% Methocel E3 LV (HPMC)
Swelling layer: 75% Polyox 205-NF (PEO)
24% Methocel K4M (HPMC)
1% Magnesium Stearate.

What is claimed is:

1. A gastric retention dosage form comprising dimethyl fumarate and one or more pharmaceutically acceptable excipients,
   wherein upon oral administration to a subject: (a) said gastric retention dosage form is retained for at least 3 hours in the stomach of the subject; and (b) the dimethyl fumarate is released from the dosage form in the gastrointestinal tract of the subject over a sustained period of time, and
   wherein said gastric retention dosage form is a swelling dosage form in the form of a swelling tablet, wherein the swelling tablet is a bilayer tablet comprising: (i) a swelling layer that does not comprise dimethyl fumarate; and (ii) an active layer comprising dimethyl fumarate.

2. The gastric retention dosage form of claim 1, wherein the swelling layer comprises one or more swelling polymers selected from the group consisting of polyethylene oxide and hydroxyalkyl alkylcellulose polymers.

3. The gastric retention dosage form of claim 1, wherein the swelling dosage form comprises: (a) dimethyl fumarate in an amount of about 20% w/w to about 80% w/w of the swellable dosage form, wherein the dimethyl fumarate is coated with a seal coat, enteric coat, or a combination thereof, and (b) one or more swelling polymers in an amount of about 10% w/w to about 50% w/w of the swellable dosage form.

4. The gastric retention dosage form of claim 3, wherein the swelling dosage form comprises dimethyl fumarate in an amount of about 50% w/w to about 60% w/w of the swellable dosage form.

5. The gastric retention dosage form of claim 1 or 3, wherein the sustained period of time is from about 2 to about 24 hours.

6. The gastric retention dosage form of claim 5, wherein the sustained period of time is from about 2 to about 16 hours.

* * * * *